US007466407B2

(12) United States Patent
Spillane et al.

(10) Patent No.: US 7,466,407 B2
(45) Date of Patent: Dec. 16, 2008

(54) PHOTONIC CRYSTAL RAMAN SENSORS AND METHODS INCLUDING THE SAME

(75) Inventors: Sean M. Spillane, Mountain View, CA (US); Raymond G. Beausoleil, Redmond, WA (US); Zhiyong Li, Redwood City, CA (US); Duncan Stewart, Menlo Park, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 79 days.

(21) Appl. No.: 11/413,877

(22) Filed: Apr. 27, 2006

(65) Prior Publication Data

US 2007/0252981 A1    Nov. 1, 2007

(51) Int. Cl.
*G01J 3/44* (2006.01)

(52) U.S. Cl. ...................................... 356/301
(58) Field of Classification Search ................ 356/301, 356/300; 359/321
See application file for complete search history.

(56) References Cited

U.S. PATENT DOCUMENTS

| | | | |
|---|---|---|---|
| 5,187,461 A | | 2/1993 | Brommer et al. |
| 5,389,943 A | | 2/1995 | Brommer et al. |
| 5,471,180 A | | 11/1995 | Brommer et al. |
| 5,999,308 A | * | 12/1999 | Nelson et al. ............... 359/321 |
| 2002/0182716 A1 | * | 12/2002 | Weisbuch et al. ......... 435/287.2 |
| 2005/0063444 A1 | * | 3/2005 | Frick ........................... 372/92 |
| 2006/0164635 A1 | * | 7/2006 | Islam et al. .................. 356/301 |

OTHER PUBLICATIONS

Adam, T.N., et al., "The Design and Fabrication of Microdisk Resonators for Terahertz Frequency Operation," Proceedings IEEE Lester Eastman Conference on High Performance Devices, 7 pages, 2002.
Borselli, Matthew, et al., "Beyond the Rayleigh scattering limit in high-Q silicon microdisks: theory and experiment," Optics Express, vol. 13, No. 5, pp. 1515-1530, Mar. 7, 2005.
Djordjev, Kostadin, et al., "High-Q Vertically Coupled InP Microdisk Resontators," IEEE Photonics Technology Letters, vol. 14, No. 3, pp. 331-333, Mar. 2002.
Djordjev, Kostadin, et al., "Study of the Effects of the Geometry on the Performance of Vertically Coupled InP Microdisk Resonators," Journal of Lightwave Technology, vol. 20, No. 8, pp. 1485-1492, Aug. 2002.
Joannopoulos, John D., et al., "Photonic Crystals, Molding the Flow of Light," Appendix D, pp. 127-129, Princeton University Press, 1995.
Kippenberg, T.J., et al., "Fabrication and coupling to planar high-Q silica disk microcavities," Applied Physics Letters, vol. 83, No. 4, pp. 797-799, Jul. 28, 2003.

* cited by examiner

*Primary Examiner*—Michael A Lyons
*Assistant Examiner*—Abdullahi Nur

(57) ABSTRACT

Raman-enhancing structures include a photonic crystal having a resonant cavity and at least one waveguide coupled to the resonant cavity. A nanostructure comprising a Raman-enhancing material is disposed proximate the resonant cavity of the photonic crystal. Raman-enhancing structures include a microdisk resonator, at least one waveguide coupled to the microdisk resonator, and a nanostructure comprising a Raman-enhancing material disposed proximate the microdisk resonator. Methods for performing Raman spectroscopy include generating radiation, guiding the radiation through a waveguide to a resonant cavity in a photonic crystal or a microdisk resonator, resonating the radiation in the resonant cavity or microdisk resonator, providing an analyte proximate the resonant cavity or microdisk resonator, subjecting the analyte to the resonating radiation, and detecting Raman scattered radiation.

21 Claims, 12 Drawing Sheets

PHOTONIC CRYSTAL RAMAN SENSORS AND METHODS INCLUDING THE SAME

FIELD OF THE INVENTION

The present invention relates to Raman spectroscopy. More particularly, the invention relates to Raman-enhancing structures that include a resonant cavity and a waveguide, Raman spectroscopy systems including such Raman-enhancing structures, and methods for performing Raman spectroscopy using such Raman-enhancing structures.

BACKGROUND OF THE INVENTION

Raman Spectroscopy

Raman spectroscopy is a well-known technique for analyzing molecules or materials. In conventional Raman spectroscopy, high intensity monochromatic radiation provided by a radiation source, such as a laser, is directed onto an analyte (or sample) that is to be analyzed. In Raman spectroscopy, the wavelength of the incident radiation typically is varied over a range of wavelengths within or near the visible region of the electromagnetic spectrum. A majority of the photons of the incident radiation are elastically scattered by the analyte. In other words, the scattered photons have the same energy, and thus the same wavelength, as the incident photons. However, a very small fraction of the photons are inelastically scattered by the analyte. Typically, only about 1 in $10^7$ of the incident photons are inelastically scattered by the analyte. These inelastically scattered photons have a wavelength that differs from the wavelength of the incident photons. This inelastic scattering of photons is termed "Raman scattering". The Raman scattered photons can have wavelengths less than, or, more typically, greater than the wavelength of the incident photons.

When an incident photon collides with the analyte, energy can be transferred from the photon to the molecules or atoms of the analyte, or from the molecules or atoms of the analyte to the photon. When energy is transferred from the incident photon to the analyte, the Raman scattered photon will have a lower energy and a corresponding longer wavelength than the incident photon. These Raman scattered photons having lower energy than the incident photons are collectively referred to in Raman spectroscopy as the "Stokes radiation." A small fraction of the analyte molecules or atoms can be in an energetically excited state when photons are incident thereon. When energy is transferred from the analyte to the incident photon, the Raman scattered photon will have a higher energy and a corresponding shorter wavelength than the incident photon. These Raman scattered photons having higher energy than the incident photons are commonly referred to in Raman spectroscopy as the "anti-Stokes radiation." The Stokes radiation and the anti-Stokes radiation collectively are referred to as the Raman scattered radiation or the Raman signal.

The Raman scattered radiation is detected by a detector that typically includes a wavelength-dispersive spectrometer and a photomultiplier for converting the energy of the impinging photons into an electrical signal. The characteristics of the electrical signal are at least partially a function of both the energy of the Raman scattered photons (as evidenced by their wavelength, frequency, or wave number) and the number of the Raman scattered photons (as evidenced by the intensity of the Raman scattered radiation). The electrical signal generated by the detector can be used to produce a spectral graph illustrating the intensity of the Raman scattered radiation as a function of the wavelength of the Raman scattered radiation. Analyte molecules and materials generate unique Raman spectral graphs. The unique Raman spectral graph obtained by performing Raman spectroscopy can be used for many purposes, including identification of an unknown analyte, or determination of physical and chemical characteristics of a known analyte.

Raman scattering of photons is a weak process. As a result, powerful, costly laser sources typically are used to generate high intensity incident radiation to increase the intensity of the weak Raman scattered radiation for detection. Surface-enhanced Raman spectroscopy (SERS) is a technique that allows for enhancement of the intensity of the Raman scattered radiation relative to conventional Raman spectroscopy. In SERS, the analyte molecules typically are adsorbed onto or placed adjacent to what is often referred to as a SERS-active structure. SERS-active structures typically include a metal surface or structure. Interactions between the analyte and the metal surface may cause an increase in the intensity of the Raman scattered radiation. The mechanism by which the intensity of the Raman scattered radiation is enhanced is not completely understood.

Several types of metallic structures have been employed in SERS techniques to enhance the intensity of Raman scattered radiation that is scattered by an analyte adjacent thereto. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface of gold or silver can enhance the Raman scattering intensity by factors of between $10^3$ and $10^6$.

Raman spectroscopy recently has been performed employing randomly oriented nanoparticles, such as nanometer scale needles, particles, and wires, as opposed to a simple roughened metallic surface. This process will be referred to herein as nano-enhanced Raman spectroscopy (NERS). Furthermore, structures comprising nanoparticles that are used to enhance the intensity of Raman scattered radiation may be referred to as NERS-active structures. The intensity of the Raman scattered photons from a molecule adsorbed on such a nanostructure can be increased by factors as high as $10^{16}$. At this level of sensitivity, NERS has been used to detect single molecules. Detecting single molecules with high sensitivity and molecular specificity is of great interest in the fields of chemistry, biology, medicine, pharmacology, and environmental science.

Hyper-Raman spectroscopy is another Raman spectroscopy technique that involves detecting higher order wavelengths of Raman scattered radiation. The hyper-Raman scattered radiation is Raman shifted relative to integer multiples of the wavelength of the incident electromagnetic radiation. Hyper-Raman scattered radiation can provide information about the analyte that cannot be obtained from simple Raman spectroscopy. The intensity of the hyper-Raman scattered radiation, however, is even less than the intensity of the Raman scattered radiation. As a result, hyper-Raman spectroscopy typically is performed using SERS-active or NERS-active structures.

Photonic Crystals

Photonic crystals are a new class of man-made materials. They are often referred to as "metamaterials." Photonic crystals are formed by dispersing a material of one dielectric constant periodically within a matrix having a different dielectric constant. A one-dimensional photonic crystal is a three-dimensional structure that exhibits periodicity in dielectric constant in only one dimension. Bragg mirrors are an example of a one-dimensional photonic crystal. The alternating thin layers have different dielectric constants and refractive indices. The combination of several thin layers forms a three-dimensional structure that exhibits periodicity in dielectric constant in only the direction orthogonal to the planes of the thin layers. No periodicity is exhibited in either of the two dimensions contained within the plane of the layers.

A two-dimensional photonic crystal can be formed by periodically dispersing rods or columns of a material of one dielectric constant within a matrix having a different dielectric constant. Two-dimensional photonic crystals exhibit periodicity in only two dimensions, i.e., the directions perpendicular to the length of the rods or columns, but no periodicity is exhibited in the direction parallel to the length of the columns.

Finally, a three-dimensional photonic crystal can be formed by periodically dispersing small spheres or other spatially confined areas of a first material having a first dielectric constant within a matrix of a second material having a second, different, dielectric constant. Three-dimensional photonic crystals exhibit periodicity in dielectric constant in all three dimensions within the crystal.

Photonic crystals may exhibit a photonic bandgap over a range of frequencies in directions exhibiting periodicity in dielectric constant. In other words, there may be a range of frequencies of electromagnetic radiation that will not be transmitted through the photonic crystal in the directions exhibiting periodicity in dielectric constant. This range of frequencies that are not transmitted is known as a photonic bandgap of the photonic crystal. No photonic bandgap is exhibited in directions that do not exhibit periodicity in dielectric constant.

When defects are introduced into the periodic dielectric structure of a photonic crystal, localized electromagnetic modes may be allowed at frequencies within the photonic bandgap. For example, resonant cavities have been formed in photonic crystals by introducing point defects into the periodic dielectric structure, and waveguides have been formed in photonic crystals by introducing line defects into the periodic dielectric structure.

BRIEF SUMMARY OF THE INVENTION

The present invention relates to Raman spectroscopy. More particularly, the invention relates to Raman-enhancing structures that include a resonant cavity and a waveguide, Raman spectroscopy systems including such Raman-enhancing structures, and methods for performing Raman spectroscopy using such Raman-enhancing structures.

In one aspect, the present invention comprises a Raman-enhancing structure. The Raman-enhancing structure includes a photonic crystal that includes a resonant cavity and at least one waveguide coupled to the resonant cavity. The Raman-enhancing structure also includes a nanostructure comprising a Raman-enhancing material disposed proximate the resonant cavity of the photonic crystal.

In yet another aspect, the present invention comprises a Raman-enhancing structure that includes a microdisk resonator, at least one waveguide coupled to the microdisk resonator, and a nanostructure comprising a Raman-enhancing material disposed proximate the microdisk resonator.

In a further aspect, the present invention comprises a method for performing Raman spectroscopy. The method includes generating electromagnetic radiation, guiding the electromagnetic radiation through a waveguide in a photonic crystal to a resonant cavity in the photonic crystal, resonating the electromagnetic radiation within the resonant cavity, providing an analyte proximate the resonant cavity, subjecting the analyte to the resonating electromagnetic radiation, and detecting Raman scattered radiation scattered by the analyte.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention relates to Raman spectroscopy. More particularly, the invention relates to Raman-enhancing structures that include a resonant cavity and a waveguide, Raman spectroscopy systems including such Raman-enhancing structures, and methods for performing Raman spectroscopy using such Raman-enhancing structures.

The term "nanoparticle" as used herein means a particle of any shape having cross-sectional dimensions of less than about 100 nanometers. Examples of nanoparticles include, but are not limited to, nanodots (including quantum dots), nanowires, nanolines, nanocolumns, and nanospheres.

The term "nanostructure" as used herein means a structure that includes one or more elements, features, or particles having cross-sectional dimensions of less than about 100 nanometers. For example, a nanostructure may include two or more nanoparticles positioned proximate to one another. As another example, a nanostructure may include a film having ridges or depressions formed in a surface thereof that have cross-sectional dimensions of less than about 100 nanometers.

The term "analyte" as used herein means any molecule, molecules, material, substance, or matter that is to be analyzed by Raman spectroscopy.

The term "Raman-enhancing material" as used herein means a material that, when formed into appropriate geometries or configurations, is capable of increasing the number of Raman scattered photons that are scattered by an analyte when the analyte is located proximate to that material, and when the analyte and material are subjected to electromagnetic radiation. Raman-enhancing materials include, but are not limited to, silver, gold, and copper. Raman-enhancing materials are used to form SERS-active structures and NERS-active structures.

The term "Raman-enhancing structure" as used herein means a structure that is capable of increasing the number of Raman scattered photons that are scattered by an analyte when the analyte is located proximate to the structure, and the analyte and structure are subjected to electromagnetic radiation. Raman-enhancing structures include SERS-active structure and NERS-active structures.

The term "resonant cavity" as used herein means any spatially confined region in a structure in which at least one wavelength of electromagnetic radiation will resonate. Resonant cavities may include, but are not limited to, regions adjacent to defects in photonic crystals, microdisk resonators, and microring resonators.

The illustrations presented herein are not meant to be actual views of any particular Ramen-enhancing structure or Raman spectroscopy system, but are merely idealized representations which are employed to describe the present invention. Additionally, elements common between figures may retain the same numerical designation.

Figure 1A:
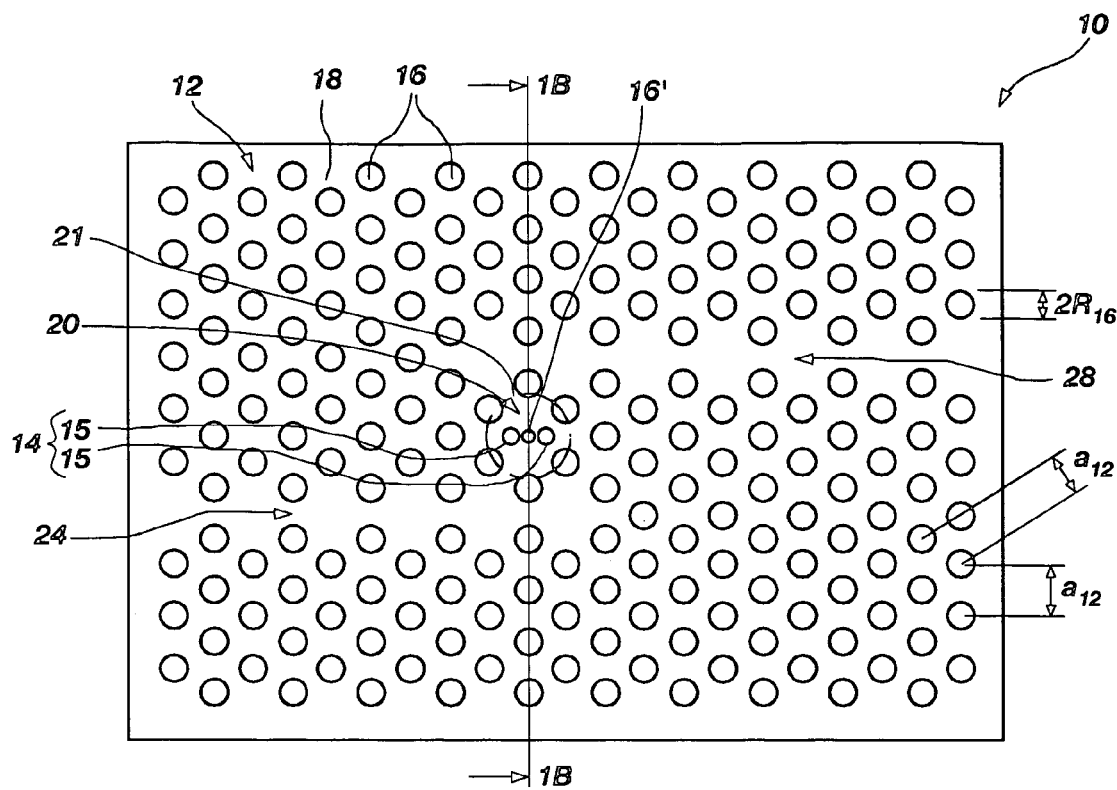
FIG. 1A is a plan view of a representative Raman-enhancing structure that embodies teachings of the present invention.
Figure 1B:
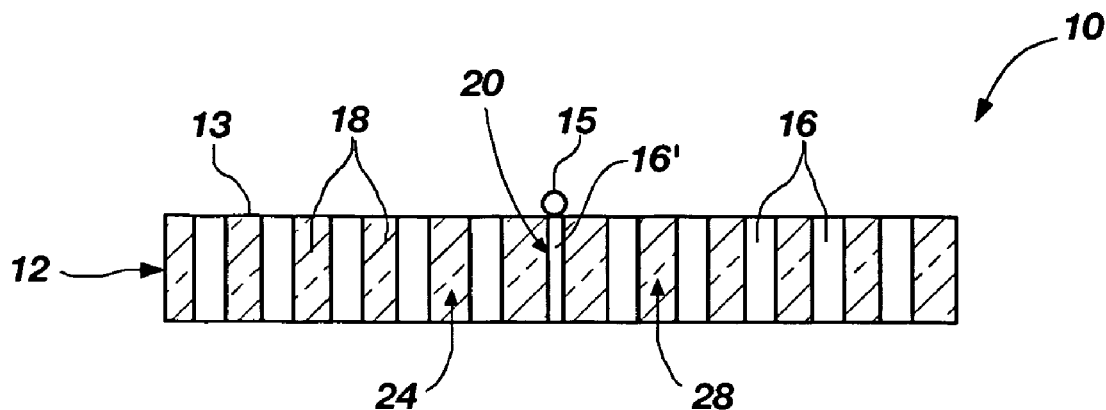
FIG. 1B is a cross-sectional view of the Raman-enhancing structure shown in FIG. 1A taken along section line 1B-1B shown therein.

A representative Raman-enhancing structure 10 that embodies teachings of the present invention is shown in FIGS. 1A-1B. The Raman-enhancing structure 10 includes a two-dimensional (2D) photonic crystal 12 and a nanostructure 14 that includes or is formed from a Raman-enhancing material. The nanostructure 14 may include at least two nanoparticles 15.

The photonic crystal 12 may include a plurality of cylindrical regions 16 dispersed periodically in an array of rows throughout a matrix 18. A majority of the cylindrical regions 16 have a uniform radius $R_{16}$. The matrix 18 exhibits a dielectric constant that differs from a dielectric constant exhibited by the cylindrical regions 16. In one particular embodiment of the invention, the matrix 18 may have a dielectric constant of about 11.4 and the cylindrical regions 16 may have a dielectric constant of about 1. For example, the matrix 18 may be formed from a semiconductor material such as GaAs and the cylindrical regions 16 may include air. Such a structure may be formed by etching the cylindrical regions 16 in a layer of GaAs using known lithographic techniques such as, for example, masking and etching. Dielectric periodicity is exhibited in the photonic crystal in directions perpendicular to a longitudinal axis (not shown) of the cylindrical regions 16.

The cylindrical regions 16 of the photonic crystal 12 may be configured in what may be referred to as a triangular lattice. The triangular lattice has a lattice constant $a_{12}$ defined as the distance separating the center of one cylindrical region 16 from the center of adjacent cylindrical regions 16. The ratio of the uniform radius $R_{16}$ of the majority of cylindrical regions 16 to the lattice constant $a_{12}$ of the photonic crystal 12 (i.e., $R_{16}/a_{12}$) may be in a range from about 0.2 to about 0.5.

The photonic crystal 12 may include a resonant cavity 20, a first waveguide 24, and a second waveguide 28. The first waveguide 24 and the second waveguide 28 each may be coupled to the resonant cavity 20. The resonant cavity 20 may be provided by including a point defect in the lattice of cylindrical regions 16. For example, a point defect may be provided by including a cylindrical region 16' having a radius that is less than the uniform radius $R_{16}$ of the majority of the cylindrical regions 16 in the lattice of the photonic crystal 12. The resonant cavity 20 may be loosely defined as the region encircled by phantom line 21. The first waveguide 24 and the second waveguide 28 may be provided by including line defects in the lattice of cylindrical regions 16. For example, a line defect may be provided by removing or failing to form cylindrical regions 16 along at least a portion of one or more rows in the photonic crystal. The first waveguide 24 and the second waveguide 28 are coupled to the resonant cavity 20 and may extend from a region adjacent the resonant cavity 20 to a lateral edge of the photonic crystal 12. The first waveguide 24 and the second waveguide 28 may be used to guide electromagnetic radiation away from the resonant cavity 20 or towards the resonant cavity 20.

The photonic crystal 12 may exhibit a photonic bandgap over a range of frequencies of electromagnetic radiation. Certain electromagnetic modes at frequencies within the photonic bandgap may be allowed within the waveguides and within the resonant cavity 20. At least one of the electromagnetic modes may resonate within the resonant cavity 20. Determining the photonic band structure of a particular photonic crystal is a complex problem that involves solving the Maxwell equations considering the periodic variation in the dielectric constant through the photonic crystal. Thus, the photonic band structure is at least partially a function of the dielectric constant of the matrix 18, the dielectric constant of the cylindrical regions 16, the uniform radius $R_{16}$, and the lattice constant $a_{12}$. Computational methods for computing the band structure of a particular photonic crystal are known in the art. An explanation of these computational methods may be found in John D. Joannopoulos, Robert D. Meade & Joshua N. Winn, *Photonic Crystals—Molding the Flow of Light*, (Princeton University Press 1995), in particular at Appendix D, the contents of which are incorporated by reference herein.

Referring to FIG. 1B, the nanoparticles 15 of the nanostructure 14 may be disposed on a surface 13 of the photonic crystal 12 adjacent the resonant cavity 20. Furthermore, each nanoparticle 15 may be configured as, for example, a sphere having a diameter in a range from about 2 nanometers to about 100 nanometers. Furthermore, each nanoparticle 15 may be formed from or include, for example, silver, gold, or copper. In alternative embodiments of the present invention, the nanostructure 14 may include a plurality of nanoparticles 15 provided on a surface 13 of the photonic crystal 12, at least some of the nanoparticles 15 being disposed adjacent the resonant cavity 20. Furthermore, the nanostructure 14 may be provided within the resonant cavity 20. For example, the nanoparticles 15 of the nanostructure 14 may be provided within the cylindrical region 16' shown in FIG. 1B.

The resonant cavity 20 may be configured to resonate Raman scattered radiation that is scattered by an analyte. In this configuration, the Raman-enhancing structure 10 may be used to perform Raman spectroscopy and to enhance the intensity of the Raman scattered radiation that is scattered by the analyte. An analyte (not shown in FIGS. 1A-1B) may be provided proximate the nanostructure 14. The analyte and the nanostructure 14 may be irradiated with incident electromagnetic radiation emitted from a radiation source (not shown in FIGS. 1A-1B). Raman scattered radiation scattered by the analyte may couple to and resonate within the resonant cavity 20. The Raman scattered radiation that is resonating within the resonant cavity 20 may couple to at least one of the first waveguide 24 and the second waveguide 28. At least some of this Raman scattered radiation may be guided from the resonant cavity 20 to a lateral edge of the photonic crystal 12 through at least one of the waveguides. At least one of the first waveguide 24 and the second waveguide 28 may be coupled to a radiation detector (not shown in FIGS. 1A-1B). The radiation detector may be used to detect the Raman scattered radiation that is traveling through the waveguides. This Raman scattered radiation may be used to identify or characterize the analyte. It should be noted that Raman scattered radiation may be scattered in all directions and could be detected from any position, such as, for example, above the surface 13 of the photonic crystal 12.

In the Raman-enhancing structure 10 shown in FIGS. 1A-1B, the resonant cavity 20 is configured to resonate Raman scattered radiation, thereby enhancing the Raman signal. In alternative embodiments of the invention, Raman-enhancing structures may include resonant cavities configured to resonate incident electromagnetic radiation and an analyte may be subjected to the resonating incident electromagnetic radiation to enhance the Raman signal.

Figure 2A:
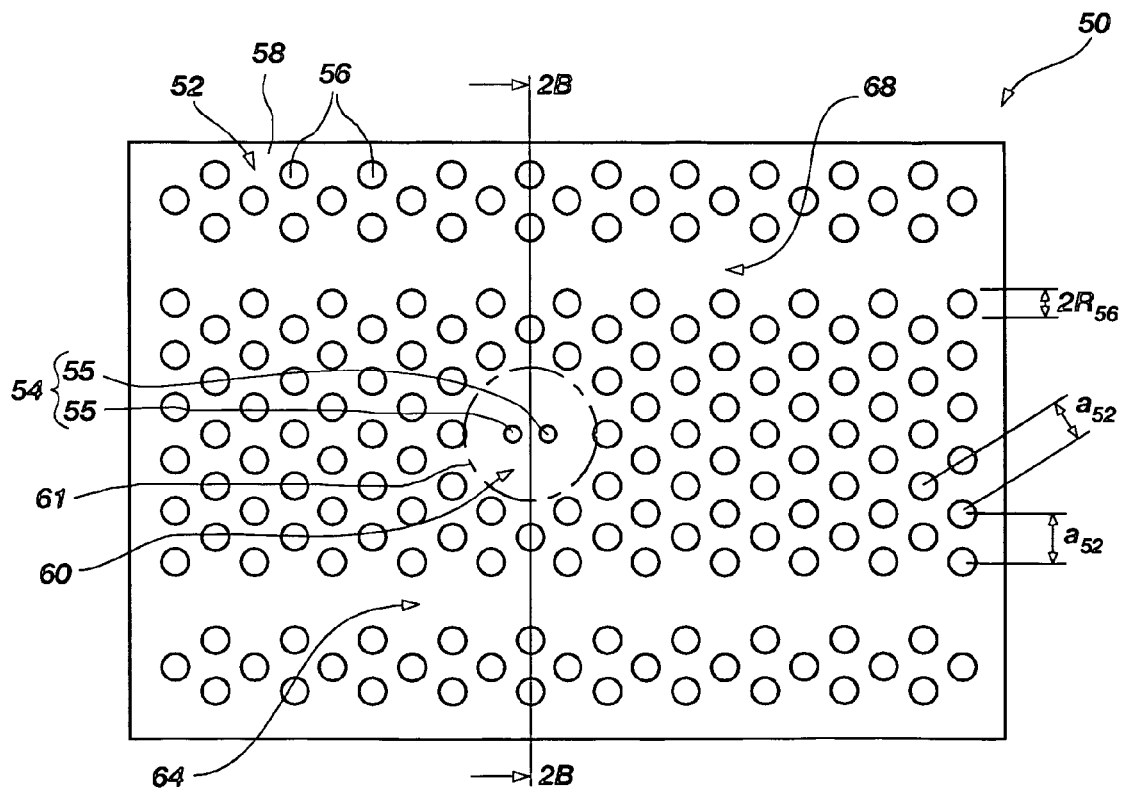
FIG. 2A is a plan view of another representative Raman-enhancing structure that embodies teachings of the present invention.
Figure 2B:
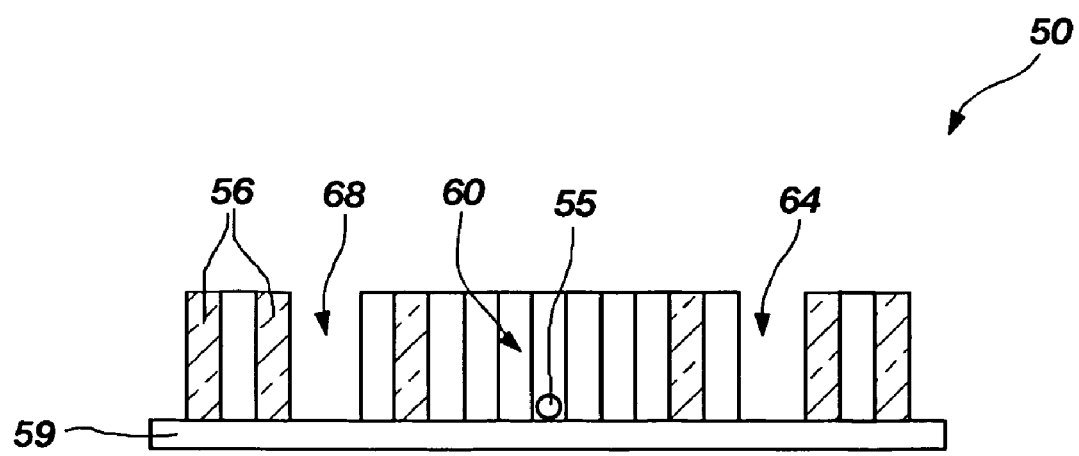
FIG. 2B is a cross-sectional view of the Raman-enhancing structure shown in FIG. 2A taken along section line 2B-2B shown therein.

Another representative Raman-enhancing structure 50 is shown in FIGS. 2A-2B. The Raman-enhancing structure 50 includes a 2D photonic crystal 52 and a nanostructure 54 that includes or is formed from a Raman-enhancing material. For example, the nanostructure 54 may include two nanoparticles 55.

The photonic crystal 52 may include a plurality of cylindrical regions 56 dispersed periodically in an array of rows throughout a matrix 58 in a triangular lattice. The matrix 58 exhibits a dielectric constant that differs from a dielectric constant exhibited by the cylindrical regions 56. A majority of the cylindrical regions have a uniform radius $R_{56}$, and the triangular lattice has a lattice constant $a_{52}$.

In one particular embodiment of the invention, the matrix 58 may have a dielectric constant of about 1 and the cylindrical regions 56 may have a dielectric constant of about 11.4. For example, the matrix 58 may be air and the cylindrical regions 56 may be formed form GaAs. In this configuration, the ratio $R_{56}/a_{52}$ may be in a range from about 0.1 to about 0.5.

The photonic crystal 52 may include a resonant cavity 60, a first waveguide 64, and a second waveguide 68. The first waveguide 64 and the second waveguide 68 may be coupled to the resonant cavity 60. The resonant cavity 60 may be provided by a point defect in the photonic crystal 52, which may be provided by, for example, removing or failing to form at least one cylindrical region 56. The resonant cavity 60 may be loosely defined as the region encircled by phantom line 61 shown in FIG. 2A. The first waveguide 64 and the second waveguide 68 may be provided by line defects in the photonic crystal 52, which may be provided by removing or failing to form a number of cylindrical regions 56 along at least a portion of one or more rows in the photonic crystal 52. The first waveguide 64 and the second waveguide 68 are coupled to the resonant cavity 60 and may extend from a lateral edge of the photonic crystal 52 to a region adjacent the resonant cavity 60. The first waveguide 64 may be configured to guide electromagnetic radiation to the resonant cavity 60 and the second waveguide 68 may be configured to guide electromagnetic radiation away from the resonant cavity 60.

Referring to FIG. 2B, the cylindrical regions 56 of the photonic crystal 52 may be formed on a substrate 59. The nanoparticles 55 of the nanostructure 54 may be disposed on the substrate 59 within the resonant cavity 60.

The photonic crystal 52 may exhibit a photonic bandgap over a range of frequencies of electromagnetic radiation. Certain electromagnetic modes at frequencies within the photonic bandgap may be allowed within the first waveguide 64 and the second waveguide 68 and within the resonant cavity 60. At least one of the electromagnetic modes may resonate within the resonant cavity 60.

The Raman-enhancing structure 50 may be used to enhance the Raman scattered radiation scattered by an analyte. An analyte may be provided proximate the resonant cavity 60 and the nanostructure 54. Electromagnetic radiation emitted from a radiation source may be coupled to one of the waveguides. The electromagnetic radiation may travel along the waveguide and into the resonant cavity 60. The electromagnetic radiation may resonate within the resonant cavity 60 resulting in high intensities of electromagnetic radiation in the region proximate the resonant cavity 60, the nanostructure 54, and the analyte. When the analyte is provided proximate the resonant cavity 60, the analyte may be subjected to intense electromagnetic radiation, and Raman scattered radiation may be scattered by the analyte. At least some of this Raman scattered radiation may be guided from the resonant cavity 60 to a lateral edge of the photonic crystal 52 through at least one of the waveguides. A radiation detector may be used to detect the Raman scattered radiation. Using the Raman-enhancing structure 50, electromagnetic radiation may be introduced into the resonant cavity 60 from either end of the first waveguide 64 or from either end of the second waveguide 68. Similarly Raman scattered radiation may be detected from either end of the first waveguide 64 or from either end of the second waveguide 68. In this configuration, different wavelengths of electromagnetic radiation could be introduced into the photonic crystal from more than one source of electromagnetic radiation, each source introducing radiation through a different end of a waveguide.

The Raman-enhancing structure 10 shown in FIGS. 1A-1B and the Raman-enhancing structure 50 shown in FIGS. 2A-2B are shown to include a first waveguide that extends parallel to a second waveguide. In alternative embodiments of the present invention, Raman-enhancing structures may include waveguides that extend in series relative to one another.

Figure 3:
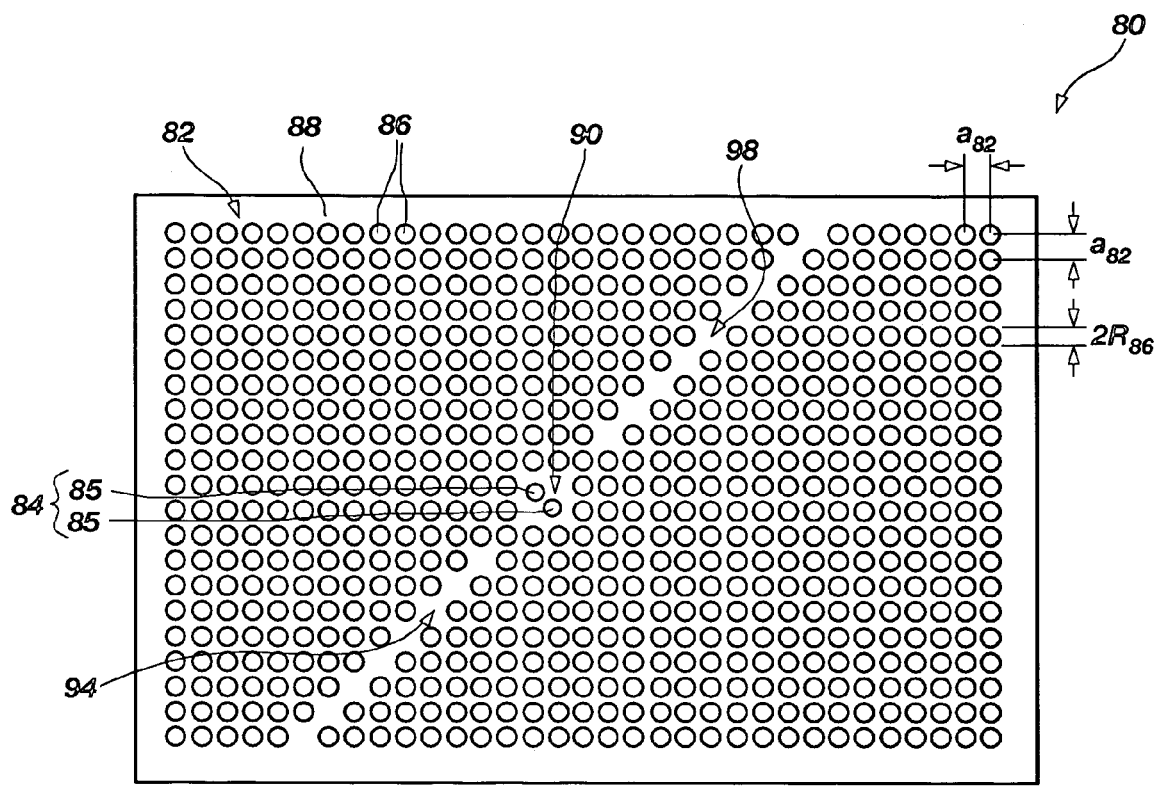
FIGS. 3-4 are plan views of representative Raman-enhancing structures that embody teachings of the present invention.

Another representative Raman-enhancing structure 80 that embodies teachings of the present invention is shown in FIG. 3. The Raman-enhancing structure 80 includes a 2D photonic crystal 82 and a nanostructure 84 that includes or is formed from a Raman-enhancing material. For example, the nanostructure 84 may include at least two nanoparticles 85.

The photonic crystal 82 may include a plurality of cylindrical regions 86 dispersed periodically in an array of rows throughout a matrix 88. A majority of the cylindrical regions have a uniform radius $R_{86}$. The cylindrical regions 86 of the photonic crystal 82 may be configured in what is often referred to as a square lattice. The square lattice has a lattice constant $a_{82}$ defined as the distance separating the center of one cylindrical region 86 from the center of adjacent cylindrical regions 86. The matrix 88 exhibits a dielectric constant that differs from the dielectric constant exhibited by the cylindrical regions 86. In one particular embodiment of the invention, the matrix 88 may have a dielectric constant of about 11.4 and the cylindrical regions 86 may have a dielectric constant of about 1. For example, the matrix 88 may be formed from a semiconductor material such as GaAs and the cylindrical regions 86 may include air. In this configuration, the ratio $R_{86}/a_{82}$ may be in a range from about 0.4 to about 0.6.

The photonic crystal 82 may include a resonant cavity 90, a first waveguide 94, and a second waveguide 98. The first waveguide 94 and the second waveguide 98 each may be coupled to the resonant cavity 90. The resonant cavity 90 may be provided by including a point defect in the lattice of cylindrical regions 86, which may be provided by removing or failing to form a number of cylindrical regions 86 in the lattice of cylindrical regions 86. For example, the resonant cavity 90 shown in FIG. 3 is provided by an absence of four cylindrical regions 86 in the lattice of cylindrical regions 86.

The first waveguide 94 and the second waveguide 98 may be provided by including line defects in the lattice of cylindrical regions 86. The first waveguide 94 and the second waveguide 98 may be coupled to the resonant cavity 90 and may extend from a lateral edge of the photonic crystal 82 to a region adjacent the resonant cavity 90. The first waveguide 94 may be configured to guide electromagnetic radiation to the resonant cavity 90 and the second waveguide 98 may be configured to guide electromagnetic radiation away from the resonant cavity 90. As seen in FIG. 3, the first waveguide 94 and the second waveguide 98 may extend in series.

The photonic crystal 82 may exhibit a photonic bandgap over a range of frequencies of electromagnetic radiation. Certain electromagnetic modes at frequencies within the photonic bandgap may be allowed within the first waveguide 94 and the second waveguide 98 and within the resonant cavity 90. At least one of the electromagnetic modes may resonate within the resonant cavity 90.

Figure 4:
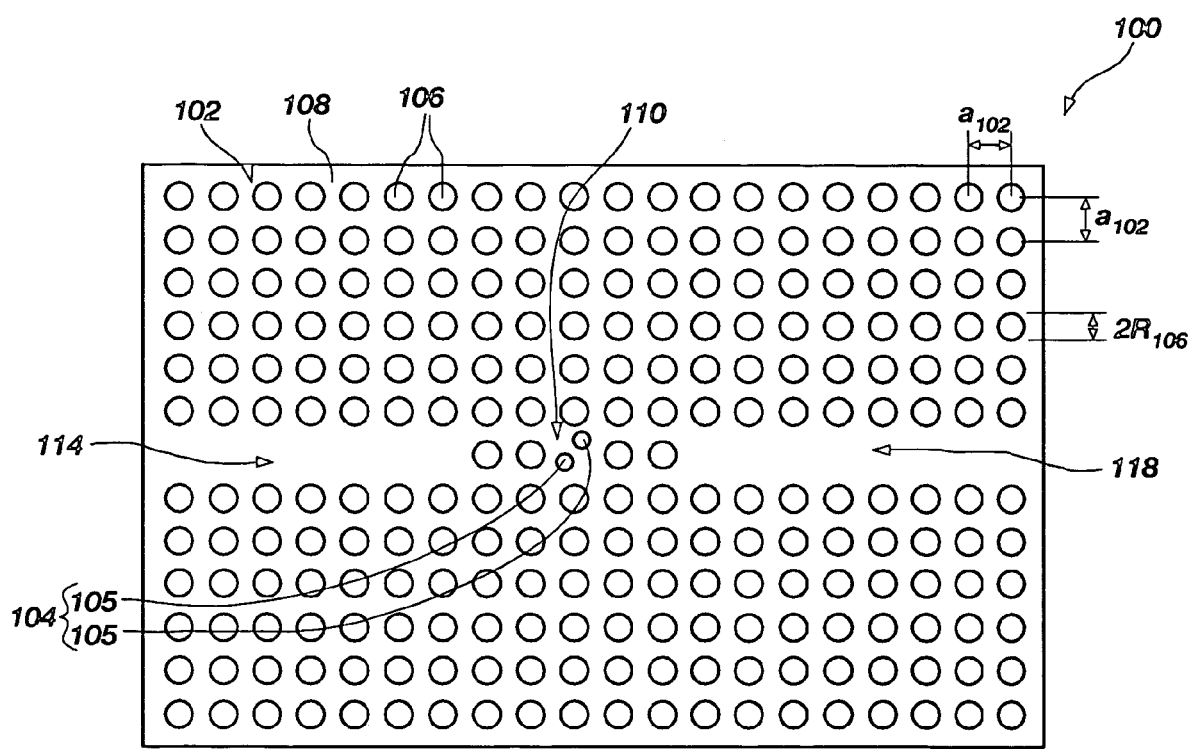

Another representative Raman-enhancing structure 100 that embodies teachings of the present invention is shown in FIG. 4. The Raman-enhancing structure 100 includes a 2D photonic crystal 102 and a nanostructure 104 that includes or is formed from a Raman-enhancing material. For example, the nanostructure may include two nanoparticles 105.

The photonic crystal 102 may include a plurality of cylindrical regions 106 dispersed periodically in an array of rows throughout a matrix 108 in a square lattice. The square lattice may have a lattice constant $a_{102}$ defined as the distance separating the center of one cylindrical region 106 from the center of adjacent cylindrical regions 106. A majority of the cylindrical regions may have a uniform radius $R_{106}$. The matrix 108 may exhibit a dielectric constant that differs from a dielectric constant exhibited by the cylindrical regions 106. For example, the photonic crystal 102 may comprise cylindrical regions 106 formed from a solid dielectric material having a dielectric constant of about 11.4 dispersed periodically in an array throughout an air matrix 108. In this configuration, the ratio $R_{106}/a_{102}$ may be in a range from about 0.1 to about 0.4. Other embodiments of Raman-enhancing structures that include a photonic crystal that exhibit a photonic bandgap are considered to be within the scope of the present invention.

The photonic crystal 102 may include a resonant cavity 110, a first waveguide 114, and a second waveguide 118. The first waveguide 114 and the second waveguide 118 each may be coupled to the resonant cavity 110. The resonant cavity 110 may be provided by including a point defect in the lattice of cylindrical regions 106, which may be provided by removing or failing to form at least one cylindrical region 106 in the lattice of cylindrical regions 106. For example, the resonant cavity 110 shown in FIG. 4 is provided by an absence of one cylindrical region 106 in the lattice of cylindrical regions 106. Alternatively, the resonant cavity 110 could be provided by including a point defect in the form of a cylindrical region having a radius smaller or larger than the uniform radius $R_{106}$ of the majority of cylindrical regions 106.

The first waveguide 114 and the second waveguide 118 may be provided by including line defects in the lattice of cylindrical regions 106. The first waveguide 114 and the second waveguide 118 may be coupled to the resonant cavity 110 and may extend from a lateral edge of the photonic crystal 102 to a region adjacent the resonant cavity 110. The first waveguide 114 may be configured to guide electromagnetic radiation to the resonant cavity 110 and the second waveguide 118 may be configured to guide electromagnetic radiation away from the resonant cavity 110. As seen in FIG. 4, the first waveguide 114 and the second waveguide 118 extend in series.

The photonic crystal 102 may exhibit a photonic bandgap over a range of frequencies of electromagnetic radiation. Certain electromagnetic modes at frequencies within the photonic bandgap may be allowed within the first waveguide 114 and the second waveguide 118 and within the resonant cavity 110. At least one of the electromagnetic modes may resonate within the resonant cavity 110. Each nanoparticle 105 of the nanostructure 104 may be disposed on a surface of the photonic crystal 102 adjacent the resonant cavity 110.

The Raman-enhancing structure 80 shown in FIG. 3 and the Raman-enhancing structure 100 shown in FIG. 4 may be used to perform Raman spectroscopy in at least two manners.

First, the resonant cavities of the photonic crystals may be configured to resonate Raman scattered radiation, and the Raman-enhancing structures may be used to perform Raman-spectroscopy as described previously herein in relation to the Raman-enhancing structure 10 shown in FIGS. 1A-1B. In particular, an analyte may be provided proximate the resonant cavity and the nanostructure comprising a Raman-enhancing material. The analyte and the Raman-enhancing material may be irradiated with incident excitation radiation. Raman scattered radiation scattered by the analyte may couple to and resonate within the resonant cavity. At least some of this Raman scattered radiation may couple to a waveguide and be guided from the resonant cavity to a lateral edge of the photonic crystal through the waveguide. A radiation detector may be used to detect the Raman scattered radiation.

Second, the resonant cavities of the photonic crystals may be configured to resonate incident electromagnetic radiation, and the Raman-enhancing structures may be used to perform Raman-spectroscopy as described previously herein in relation to the Raman-enhancing structure 50 shown in FIGS. 2A-2B. In particular, an analyte may be provided proximate the resonant cavity and the nanostructure comprising a Raman-enhancing material. Electromagnetic radiation emitted from a radiation source may be coupled to one of the waveguides. The electromagnetic radiation may travel along the waveguide and into the resonant cavity. The electromagnetic radiation may resonate within the resonant cavity resulting in high intensities of electromagnetic radiation in the region proximate the resonant cavity, the nanostructure, and the analyte. When the analyte is provided proximate the resonant cavity, the analyte may be subjected to intense electromagnetic radiation, and Raman scattered radiation may be scattered by the analyte. At least some of this Raman scattered radiation may be guided from the resonant cavity to a lateral edge of the photonic crystal through the other waveguide. A radiation detector may be used to detect the Raman scattered radiation.

It should be understood that the Raman-enhancing structure 10 shown in FIGS. 1A-1B and the Raman-enhancing structure 50 shown in FIGS. 2A-2B each may be used to perform Raman spectroscopy in each of the manners described in the immediately preceding paragraphs.

Figure 5A:
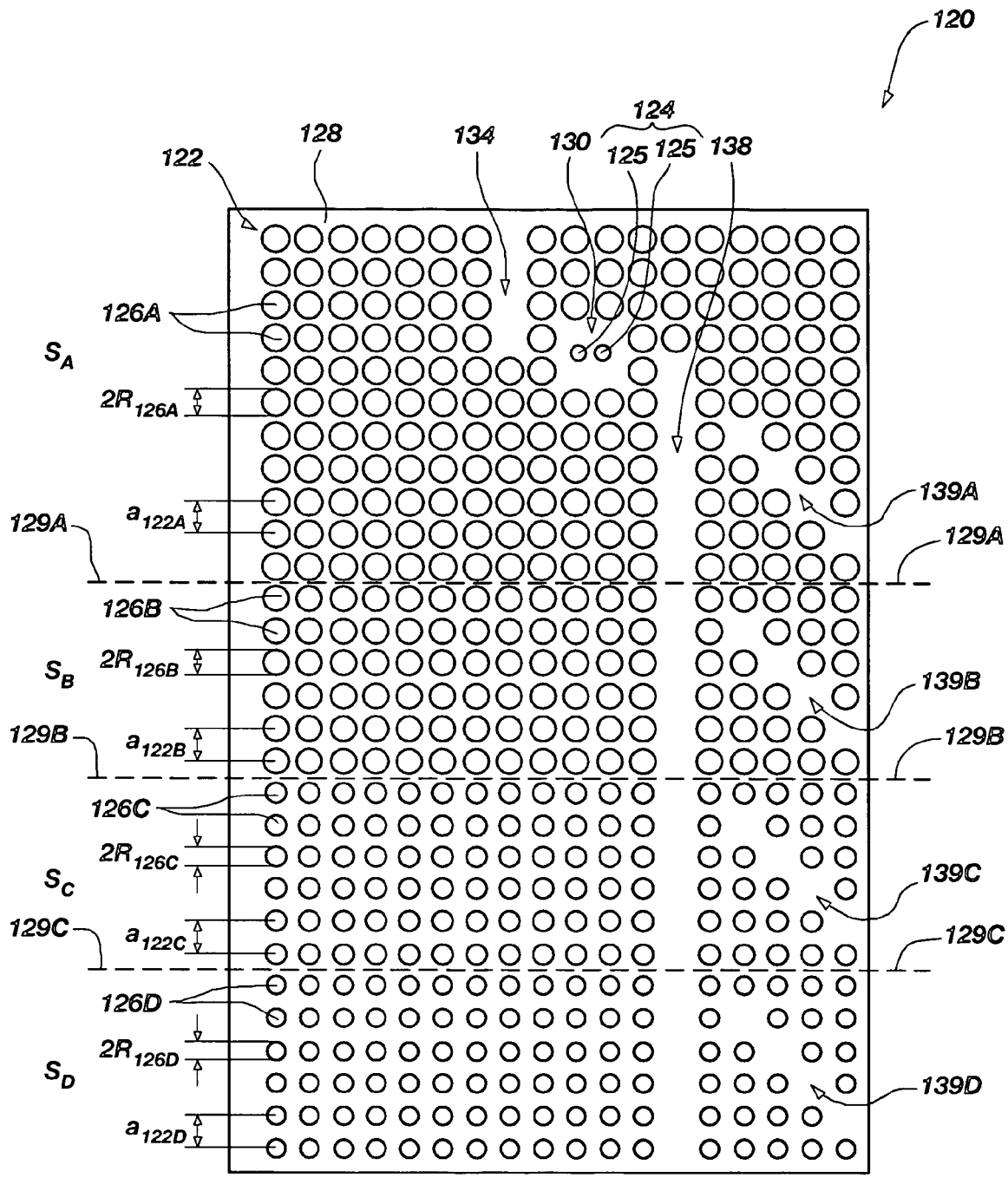
FIG. 5A is a plan view of another representative Raman-enhancing structure that embodies teachings of the present invention.
Figure 5B:
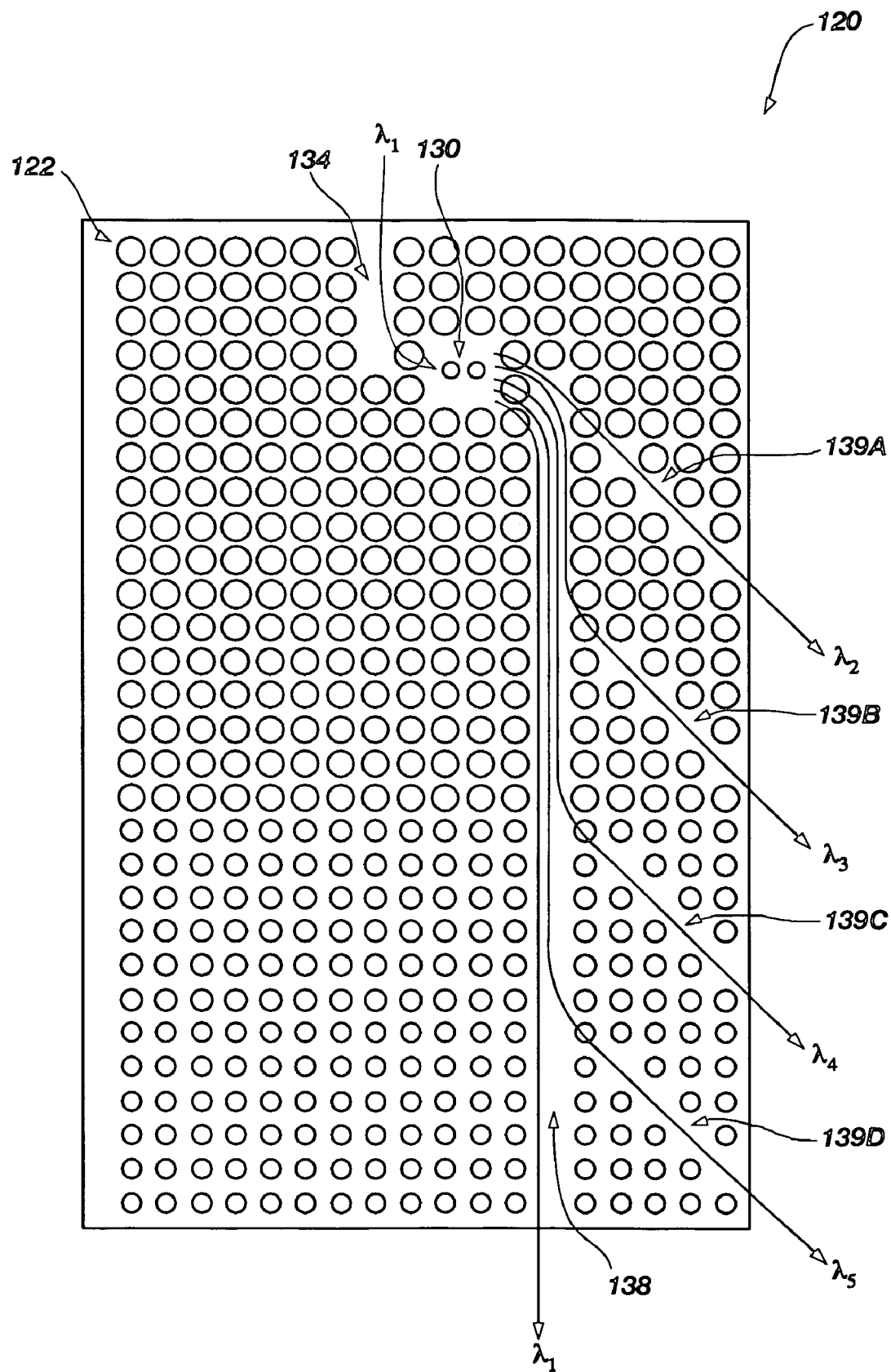
FIG. 5B is another plan view of the Raman-enhancing structure shown in FIG. 5A.

Another representative Raman-enhancing structure 120 that embodies teachings of the present invention is shown in FIGS. 5A-5B. The Raman-enhancing structure 120 includes a 2D photonic crystal 122 and a nanostructure 124 that includes or is formed from a Raman-enhancing material. For example, the nanostructure 124 may include two or more nanoparticles 125.

The photonic crystal 122 may include a plurality of cylindrical regions dispersed periodically in a square lattice throughout a matrix 128. The matrix 128 exhibits a dielectric constant that differs from a dielectric constant exhibited by the cylindrical regions. For example, the cylindrical regions may comprise a dielectric material, such as alumina, and the matrix 128 may be air.

The photonic crystal 122 may include a resonant cavity 130, an input waveguide 134, and an output waveguide 138. The input waveguide 134 and the output waveguide 138 are coupled to the resonant cavity 130. The input waveguide 134 is configured to guide electromagnetic radiation to the resonant cavity 130 and the output waveguide 138 is configured to guide electromagnetic radiation away from the resonant cavity 130. The photonic crystal 122 also includes four secondary output waveguides 139A, 139B, 139C, and 139D, which are discussed in further detail below.

The photonic crystal 122 shown in FIG. 5 includes a first section $S_A$, a second section $S_B$, a third section $S_C$, and a fourth section $S_D$. A first imaginary line 129A separates first section $S_A$ from second section $S_B$, a second imaginary line 129B separates second section $S_B$ from third section $S_C$, and a third imaginary line 129C separates third section $S_C$ from fourth section $S_D$. Each section of the photonic crystal 122 may include cylindrical regions that have a uniform radius different from the uniform radius of the cylindrical regions of the other sections. Furthermore, each section of the photonic crystal 122 may have a lattice constant that differs from the lattice constant of the other sections.

For example, the first section $S_A$ of the photonic crystal 122 may include a plurality of cylindrical regions 126A having a uniform radius $R_{126A}$. The lattice within the first section $S_A$ of the photonic crystal 122 may have a lattice constant $a_{122A}$. The second section $S_B$ of the photonic crystal 122 may include a plurality of cylindrical regions 126B having a uniform radius $R_{126B}$. The lattice within the second section $S_B$ of the photonic crystal 122 may have a lattice constant $a_{122B}$. Similarly, the third section $S_C$ of the photonic crystal 122 may include a plurality of cylindrical regions 126C having a uniform radius $R_{126C}$. The lattice within the third section $S_c$ of the photonic crystal 122 may have a lattice constant $a_{122C}$. Finally, the fourth section $S_D$ of the photonic crystal 122 may include a plurality of cylindrical regions 126D having a uniform radius $R_{126D}$. The lattice within fourth section $S_D$ of the photonic crystal 122 may have a lattice constant $a_{122D}$.

In the embodiment of the present invention shown in FIG. 5, the lattice constant is equal in each of the sections of the photonic crystal 122. In other words, $a_{122A}=a_{122B}=a_{122C}=a_{122D}$. However, the uniform radius $R_{126A}$ of the cylindrical regions 126A in the first section $S_A$ is larger than the uniform radius $R_{126B}$ of the cylindrical regions 126B in the second section $S_B$. Similarly, the uniform radius $R_{126B}$ of the cylindrical regions 126B in the second section $S_B$ is larger than the uniform radius $R_{126C}$ of the cylindrical regions 126C in the third section $S_C$. Finally, the uniform radius $R_{126C}$ of the cylindrical regions 126C in the third section $S_C$ is larger than the uniform radius $R_{126D}$ of the cylindrical regions 126D in the fourth section $S_D$. In other words, $R_{126A}>R_{126B}>R_{126C}>R_{126D}$. By varying parameters of the photonic crystal that affect the photonic band structure of the photonic crystal in each of the sections $S_A$, $S_B$, $S_C$, and $S_D$, the photonic crystal may exhibit a different band structure in each of the sections of the photonic crystal. This may be referred to as "chirping" the photonic crystal structure. The photonic crystal may be chirped by varying other parameters than just the uniform radius of the cylindrical regions. In alternative embodiments of the present invention, the uniform radius of the cylindrical regions could be equal in each of the sections $S_A$, $S_B$, $S_C$, and $S_D$, and the lattice constant could vary between the sections $S_A$, $S_B$, $S_C$, and $S_D$. Furthermore, both the uniform radius of the cylindrical regions and the lattice constant could vary between the sections $S_A$, $S_B$, $S_C$, and $S_D$. In other words, the photonic band structure of the photonic crystal 122 may be varied between sections by varying the lattice constant between sections, or by changing the dielectric constant of the cylindrical regions between sections $S_A$, $S_B$, $S_C$, and $S_D$, or by some combination of the above.

A secondary output waveguide that is coupled to the main output waveguide 138 may be provided in each of the sections $S_A$, $S_B$, $S_C$, and $S_D$ of the photonic crystal 122. As seen in FIG. 5A, the first section $S_A$ of the photonic crystal 122 may include a secondary output waveguide 139A that is coupled to the main output waveguide 138 and extends to a lateral edge of the photonic crystal 122. The second section $S_B$ of the photonic crystal 122 may include a secondary output waveguide 139B that is coupled to the main output waveguide 138 and extends to a lateral edge of the photonic crystal 122. Similarly, the third section $S_C$ of the photonic crystal 122 may include a secondary output waveguide 139C that is coupled to the main output waveguide 138 and extends to a lateral edge of the photonic crystal 122. Finally, the fourth section $S_D$ of the photonic crystal 122 may include a secondary output waveguide 139D that is coupled to the main output waveguide 138 and extends to a lateral edge of the photonic crystal 122.

Due to the difference in photonic band structure in each of the sections of the photonic crystal 122, each secondary output waveguide may guide different wavelengths of electromagnetic radiation. This allows the photonic crystal 122 to include waveguides configured to guide electromagnetic radiation at different wavelengths.

As shown in FIG. 5B, incident electromagnetic radiation $\lambda_1$ may be guided to the resonant cavity 130 of the photonic crystal 122 through the input waveguide 134. The electromagnetic radiation $\lambda_1$ may couple to and resonate within the resonant cavity 130. If the nanostructure 124 comprising a Ramen-enhancing material and an analyte are provided within or proximate to the resonant cavity 130, Raman scattered radiation may be scattered by the analyte. The Raman scattered radiation may include radiation at several different wavelengths, such as, for example, $\lambda_2$, $\lambda_3$, $\lambda_4$, and $\lambda_5$. Both the incident electromagnetic radiation $\lambda_1$ and the Raman scattered radiation $\lambda_2$, $\lambda_3$, $\lambda_4$, and $\lambda_5$ may couple to the main output waveguide 138. As seen in FIG. 5B, each of the secondary output waveguides may be configured to guide only particular wavelengths of radiation. For example the secondary output waveguide 139A may be configured to guide wavelength $\lambda_2$, the secondary output waveguide 139B may be configured to guide wavelength $\lambda_3$, the secondary output waveguide 139C may be configured to guide wavelength $\lambda_4$, and the secondary output waveguide 139D may be configured to guide wavelength $\lambda_5$. In this configuration, the incident electromagnetic radiation $\lambda_1$ may be guided through the length of the main output waveguide 138 and at least some of the wavelengths of Raman scattered radiation $\lambda_2$, $\lambda_3$, $\lambda_4$, and $\lambda_5$ may be detected from the secondary output waveguides 139A, 139B, 139C, and 139D.

In an alternative embodiment of the present invention, the resonant cavity 130 of the photonic crystal 122 shown in FIGS. 5A-5B may be configured to resonate Raman scattered radiation. In this configuration, the Raman-enhancing structure 120 could be used to perform Raman spectroscopy by providing an analyte adjacent the nanoparticles 125 and irradiating the analyte and the nanoparticles with incident electromagnetic radiation from above the photonic crystal 122 (i.e., the incident electromagnetic radiation is not guided to the resonant cavity 130 or the analyte through the waveguide 134). Raman scattered radiation scattered by the analyte may couple to and resonate within the resonant cavity 130. This resonating Raman scattered radiation may couple to the waveguide 138 and be guided thereby to a radiation detector.

Figure 6A:
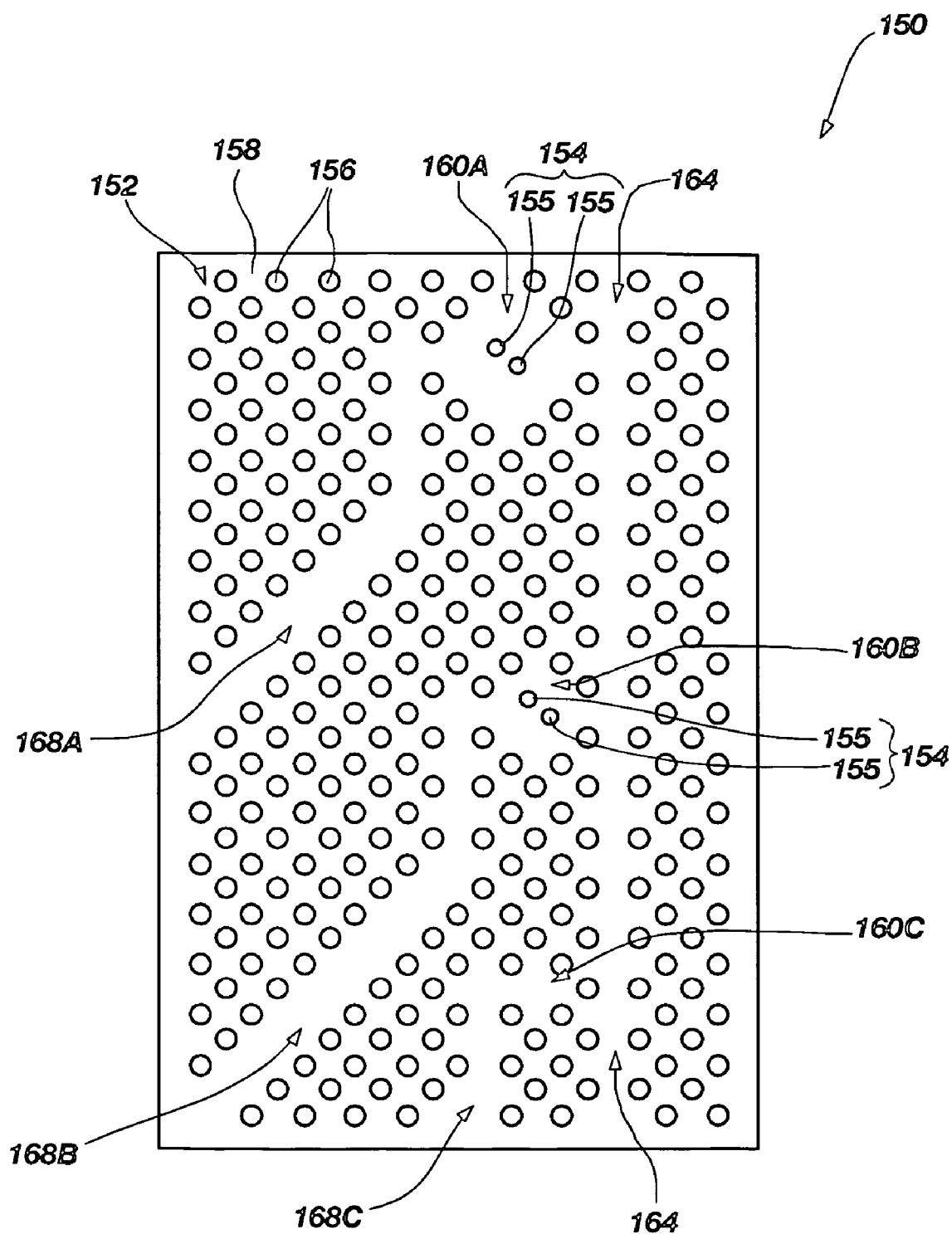
FIG. 6A is a plan view of another representative Raman-enhancing structure that embodies teachings of the present invention.
Figure 6B:
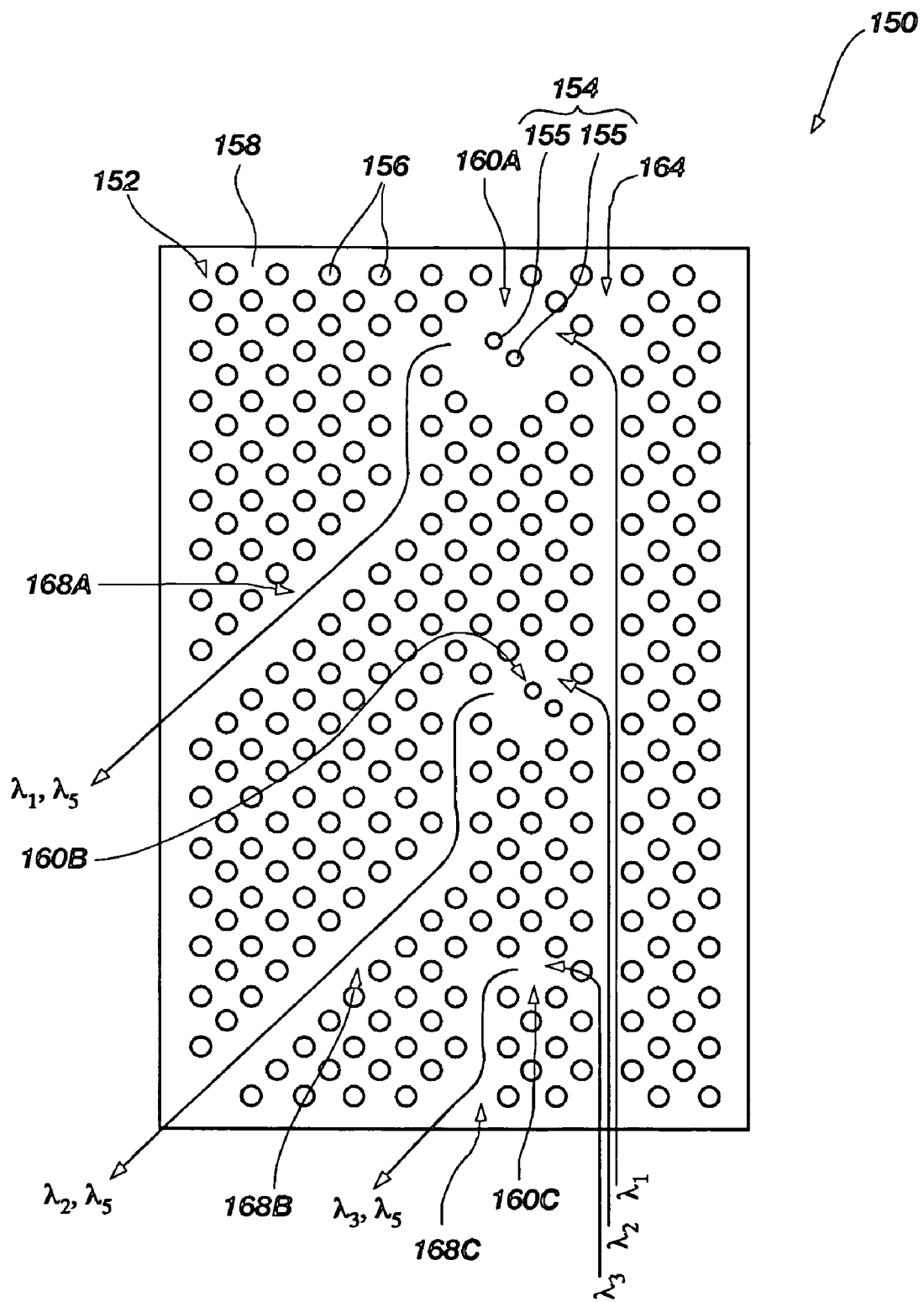
FIG. 6B is another plan view of the Raman-enhancing structure shown in FIG. 6A.

Another representative Raman-enhancing structure 150 that embodies teachings of the present invention is shown in FIGS. 6A-6B. The Raman-enhancing structure 150 includes a 2D photonic crystal 152 and a nanostructure 154 that includes or is formed from a Raman-enhancing material. For example, the nanostructure 154 may include two or more nanoparticles 155. The photonic crystal 152 may include a plurality of cylindrical regions 156 dispersed periodically in a square lattice throughout a matrix 158. The matrix 158 exhibits a dielectric constant that differs from a dielectric constant exhibited by the cylindrical regions 156. For example, the cylindrical regions may comprise a dielectric material such as a polymer, and the matrix 128 may be air.

In contrast to the previously described Raman-enhancing structures, the Raman-enhancing structure 150 includes a plurality of resonant cavities. For example, the Raman-enhancing structure 150 may include a first resonant cavity 160A, a second resonant cavity 160B, and a third resonant cavity 160C. Each of the resonant cavities may be configured to resonate different wavelengths of electromagnetic radiation. A nanostructure 154 may be provided in or adjacent to at least one of the resonant cavities. For example, nanoparticles 155 comprising a Raman-enhancing material may be provided in the first resonant cavity 160A and in the second resonant cavity 160B.

The Raman-enhancing structure 150 may include a main waveguide 164 coupled to each of the first resonant cavity 160A, the second resonant cavity 160B, and third resonant cavity 160C. The main waveguide may be provided by including a line defect in the lattice of the photonic crystal 152. The Raman-enhancing structure 150 may further include a plurality of secondary waveguides. Each secondary waveguide may be coupled to at least one of the resonant cavities. For example, the Raman-enhancing structure 150 may include a first secondary waveguide 168A that is coupled to the first resonant cavity 160A, a second secondary waveguide 168B that is coupled to the second resonant cavity 160B, and a third secondary waveguide 168C that is coupled to the third resonant cavity 160C.

The Raman-enhancing structure 150 may be used to conduct Raman spectroscopy in a manner substantially similar to that described previously herein. Referring to FIG. 6B, electromagnetic radiation comprising one or more wavelengths of electromagnetic radiation may be provided in the main waveguide 164 of the Raman-enhancing structure 150. For example, electromagnetic radiation comprising at least three wavelengths of electromagnetic radiation $\lambda_1$, $\lambda_2$, and $\lambda_3$ may be introduced into the main waveguide 164. The first resonant cavity 160A may be configured to resonate electromagnetic radiation at wavelength $\lambda_1$, the second resonant cavity 160B may be configured to resonate electromagnetic radiation at wavelength $\lambda_2$, and the third resonant cavity 160C may be configured to resonate electromagnetic radiation at wavelength $\lambda_3$.

An analyte may be placed in or adjacent to each of the first resonant cavity 160A, the second resonant cavity 160B, and the third resonant cavity 160C. An analyte disposed within or proximate to the first resonant cavity 160A may be subjected to the electromagnetic radiation at wavelength $\lambda_1$, an analyte disposed within or proximate to the second resonant cavity 160B may be subjected to the electromagnetic radiation at wavelength $\lambda_2$, and an analyte disposed within or proximate to the third resonant cavity 160C may be subjected to the electromagnetic radiation at wavelength $\lambda_3$. Raman scattered radiation $\lambda_S$ scattered by an analyte disposed within or proximate to the first resonant cavity 160A may be coupled to the first secondary waveguide 168A, Raman scattered radiation $\lambda_S$ scattered by an analyte disposed within or proximate to the second resonant cavity 160B may be coupled to the second secondary waveguide 168B, and Raman scattered radiation $\lambda_S$ scattered by an analyte disposed within or proximate to the third resonant cavity 160C may be coupled to the third secondary waveguide 168C.

In this configuration, Raman spectroscopy may be performed on an analyte using electromagnetic radiation at different wavelengths simultaneously. Furthermore, the Raman scattered radiation that originates from each of the different wavelengths of incident radiation may be collected separately. The resonant cavities may subject the analyte to electromagnetic radiation at increased intensities, which may result in a stronger or enhanced Raman signal. Furthermore, the Raman signal may be further strengthened or enhanced by providing a nanostructure, such as two or more nanoparticles, comprising a Raman-enhancing material within or proximate to the resonant cavities.

In an alternative embodiment of the present invention, each of the resonant cavities 160A, 160B, and 160C of the photonic crystal 152 shown in FIGS. 6A-6B may be configured to resonate Raman scattered radiation. In this configuration, the Raman-enhancing structure 150 could be used to perform Raman spectroscopy by providing an analyte adjacent each of the resonant cavities and nanostructures and irradiating the analyte and the nanostructures with incident electromagnetic radiation from above the photonic crystal 152 (i.e., the incident electromagnetic radiation is not guided to the resonant cavities or the analyte through a waveguide). Raman scattered radiation scattered by the analyte may couple to and resonate within at least one of the resonant cavities 160A, 160B, and 160C. This resonating Raman scattered radiation may couple to at least one of the waveguides of the photonic crystal 152 and be guided thereby to a radiation detector. If the Raman-enhancing structure 150 is provided with a plurality of resonant cavities, each configured to resonate different wavelengths of Raman scattered radiation, an analyte may be provided adjacent the resonant cavities and irradiated with incident radiation. The resonant cavities that "light up" or resonate radiation could be identified to determine the wavelengths of the Raman scattered radiation. Knowledge regarding the wavelengths of the Raman scattered radiation may be used to identify or characterize the analyte.

While each of the previously described embodiments of the present invention comprise a photonic crystal that include at least one resonant cavity and at least one waveguide coupled to the resonant cavity, other embodiments of the present invention include at least one resonant cavity and at least one waveguide that are not formed in a photonic crystal.

Figure 7A:
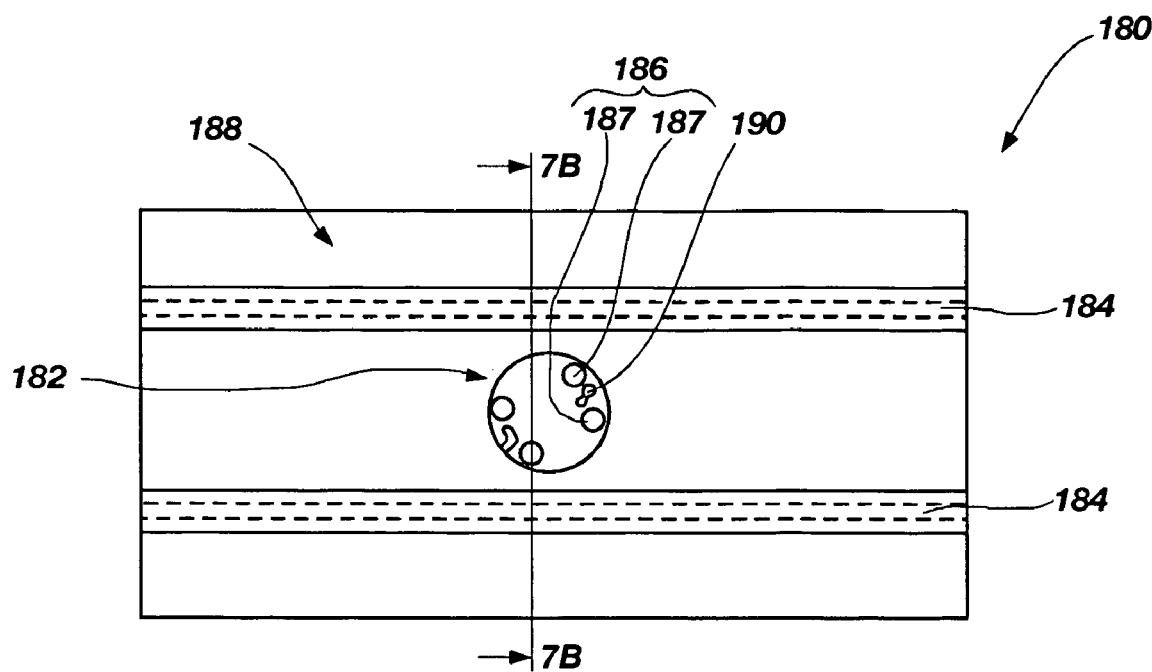
FIG. 7A is a is plan view of another representative Raman-enhancing structure that embodies teachings of the present invention.
Figure 7B:
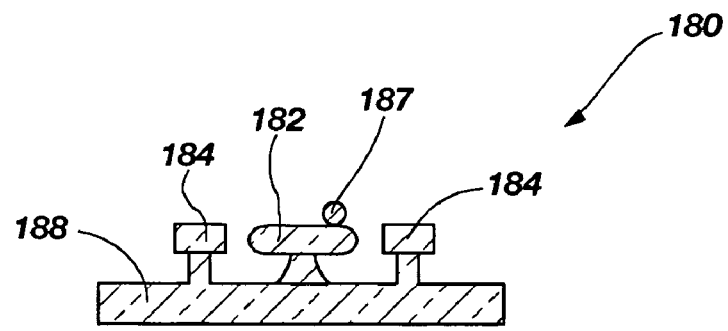
FIG. 7B is a cross-sectional view of the Raman-enhancing structure shown in FIG. 7A taken along section line 7B-7B shown therein.

A representative Raman-enhancing structure 180 that embodies teachings of the present invention is shown in FIGS. 7A-7B. The Raman-enhancing structure 180 may include a microdisk resonator 182, at least one waveguide 184 coupled to the microdisk resonator 182, and a nanostructure 186 comprising a Raman-enhancing material disposed proximate to the microdisk resonator 182. For example, the nanostructure 186 may include at least two nanoparticles 187. As seen in FIGS. 7A-7B, the Raman-enhancing structure 180 may include two parallel waveguides 184 disposed on opposite sides of the microdisk resonator 182.

The microdisk resonator 182 and the waveguides 184 may be formed on a substrate 188. For example, the substrate 188 may comprise silicon and the microdisk resonator 182 and the waveguides 184 may comprise either silicon or silica. Other materials including, but not limited to, InP and GaAs may be used to form one or more of the substrate 188, the microdisk resonator 182, and the waveguides 184. Well known lithographic techniques may be used to form such structures.

As seen in FIG. 7B, the nanoparticles 187 comprising a Raman-enhancing material may be provided, for example, on a surface of the microdisk resonator 182. In the embodiment of the present invention shown in FIGS. 7A-7B, four nanoparticles 187 comprising a Raman-enhancing material are provided on a surface of the microdisk resonator 182.

In this configuration, the Raman-enhancing structure 180 may be used to conduct Raman spectroscopy in a manner similar to that previously described. In particular, an analyte 190 (FIG. 7A) may be provided adjacent the microdisk resonator 182 and the nanoparticles 187 of the nanostructure 186. Electromagnetic radiation provided by a radiation source may be coupled to one of the waveguides 184 from an end thereof. The electromagnetic radiation may couple to and resonate within the microdisk resonator 182. It should be understood that the resonant frequencies of the microdisk resonator 182 may be at least partially a function of the dimensions of the microdisk resonator 182. The analyte 190 and the nanoparticles 187 may be subjected to the resonating electromagnetic radiation. Raman scattered radiation scattered by the analyte 190 may couple to at least one of the waveguides 184 and may be detected from an end of that waveguide 184. It is not necessary to detect Raman scattered radiation from a waveguide. Alternatively, the Raman scattered radiation could be detected from any position or direction proximate the analyte 190 since the Raman scattered radiation may be scattered in all directions. However, it may be desirable to guide the Raman scattered radiation from the analyte 190 to a detector (not shown) through a waveguide 184.

The microdisk resonator 182 may enhance the intensity of the Raman signal generated by Raman scattered radiation scattered by the analyte 190. Providing a nanostructure 186 comprising a Raman-enhancing material adjacent the microdisk resonator 182 and the analyte 190 may further enhance the Raman signal.

In alternative embodiments of the present invention, the microdisk resonator 182 could be vertically coupled to a waveguide, such as an optical fiber, as opposed to being laterally coupled to the waveguide. In such a configuration, the waveguide may pass underneath at least a portion of the microdisk resonator 182 instead of passing laterally beside the microdisk resonator 182. Furthermore, the Raman-enhancing structure may comprise a microring resonator instead of a microdisk resonator.

Figure 8:
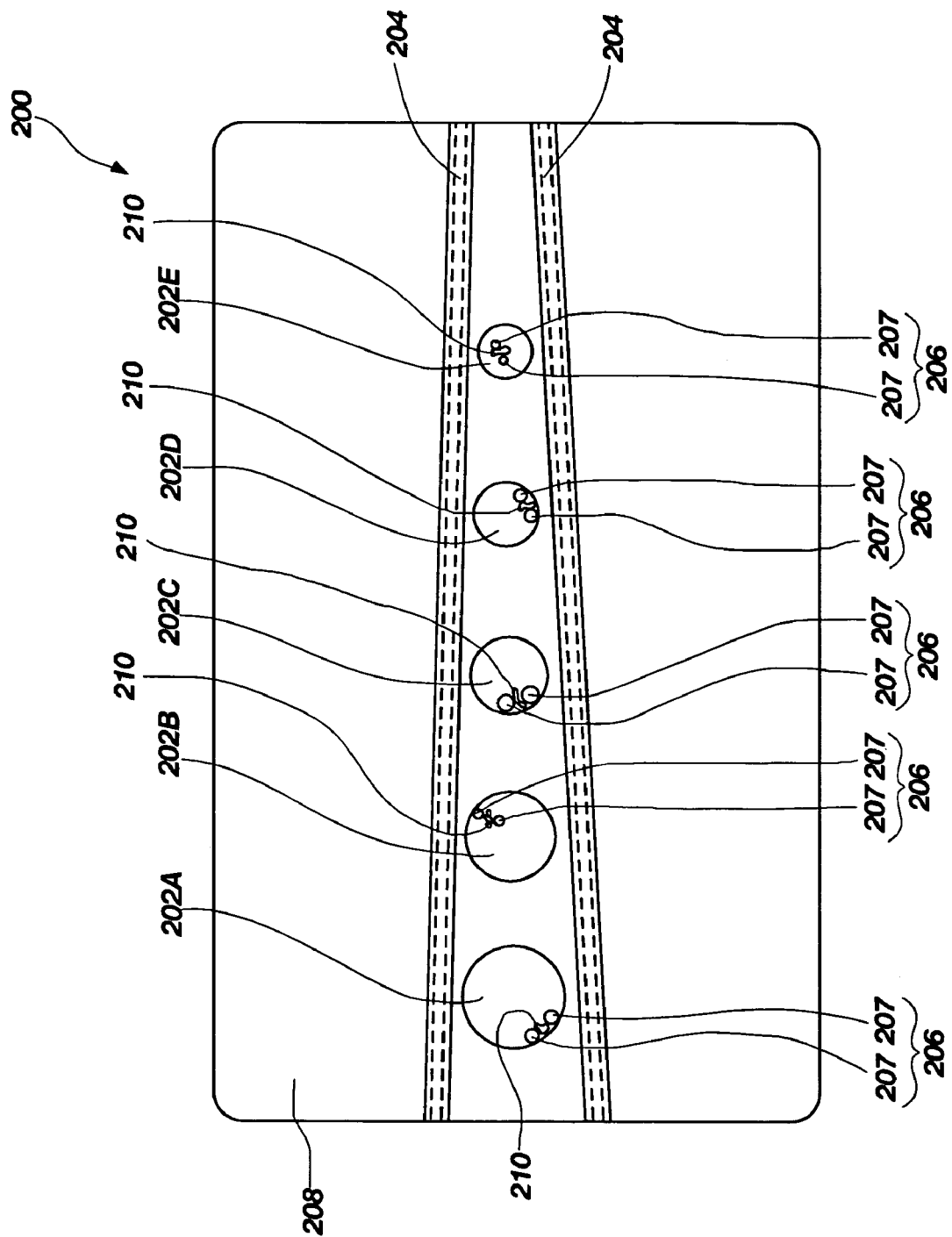
FIG. 8 is a plan view of another representative Raman-enhancing structure that embodies teachings of the present invention.

Another representative Raman-enhancing structure 200 that embodies teachings of the present invention is shown in FIG. 8. The Raman-enhancing structure 200 may include a plurality of microdisk resonators. For example, the Raman-enhancing structure 200 may include a first microdisk resonator 202A, a second microdisk resonator 202B, a third microdisk resonator 202C, a fourth microdisk resonator 202D, and a fifth microdisk resonator 202E. Each of the microdisk resonators may be configured to resonate different wavelengths of electromagnetic radiation. For example, the diameters of the microdisk resonators may be varied, as illustrated in FIG. 8. In FIG. 8, the first microdisk resonator 202A has the largest diameter and the fifth microdisk resonator 202E has the smallest diameter. Each of the second microdisk resonator 202B, the third microdisk resonator 202C, and the fourth microdisk resonator 202D has a diameter between those of the first and fifth microdisk resonators.

The Raman-enhancing structure 200 further may include at least one waveguide 204 coupled to each of the microdisk resonators. A nanostructure 206 comprising a Raman-enhancing material may be disposed proximate to each of the microdisk resonators. For example, each nanostructure 206 may comprise two or more nanoparticles 207. As seen in FIG. 8, the Raman-enhancing structure 200 may include two waveguides 204 disposed on opposite sides of the microdisk resonators.

In this configuration, the Raman-enhancing structure 200 may be used to conduct Raman spectroscopy in manners similar to those previously described. In particular, an analyte 210 may be provided adjacent to at least one of the microdisk resonators 202A, 202B, 202C, 202D, and 202E and the nanoparticles 207. Electromagnetic radiation may be provided in one of the waveguides 204 from an end thereof. The electromagnetic radiation may couple to and resonate within at least one of the microdisk resonators. If the electromagnetic radiation comprises a plurality of wavelengths of electromagnetic radiation, electromagnetic radiation may resonate within each of the microdisk resonators. The analyte 210 and the nanoparticles 207 of the nanostructure 206 may be subjected to the electromagnetic radiation resonating within the microdisk resonators. Raman scattered radiation scattered by the analyte 210 may couple to at least one of the waveguides 204 and may be detected from an end thereof. As previously discussed, it is not necessary to detect Raman scattered radiation from a waveguide, and the Raman scattered radiation could be detected from any position or direction proximate the analyte 210.

Alternatively, the microdisk resonators may each be configured to resonate Raman scattered radiation. An analyte 210 may be provided adjacent to at least one of the microdisk resonators 202A, 202B, 202C, 202D, and 202E and the nanoparticles 207 of the nanostructures 206. The analyte 210 and the nanoparticles 207 may be irradiated with incident electromagnetic radiation. Raman scattered radiation scattered by the analyte 210 may couple to and resonate within at least one of the microdisk resonators. The Raman scattered radiation may couple to at least one of the waveguides 204 and may be detected from an end thereof.

Raman-enhancing structures that embody teachings of the present invention can be used in Raman spectroscopy systems to perform Raman spectroscopy on an analyte. A representative Raman spectroscopy system 220 that embodies teachings of the present invention is illustrated schematically in FIG. 9. The Raman spectroscopy system 220 may include an electromagnetic radiation source 222 configured to emit incident electromagnetic radiation 224, a Raman-enhancing structure, and an electromagnetic radiation detector 226 configured to detect Raman scattered radiation 228. For example, the Raman spectroscopy system may include the Raman-enhancing structure 10 shown in FIGS. 1A-1B, the Raman-enhancing structure 50 shown in FIGS. 2A-2B, the Raman-enhancing structure 80 shown in FIG. 3, the Raman-enhancing structure 100 shown in FIG. 4, the Raman-enhancing structure 120 shown in FIGS. 5A-5B, the Raman-enhancing structure 150 shown in FIGS. 6A-6B, the Raman-enhancing structure 180 shown in FIGS. 7A-7B, or the Raman-enhancing structure 200 shown in FIG. 8. The Raman spectroscopy system 220 also may include various optical components 230, such as, for example, lenses and filters, positioned between the radiation source 222 and the Raman-enhancing structure, and positioned between the Raman-enhancing structure and the detector 148.

The radiation source 222 may include any suitable source for emitting radiation at a desired wavelength and may be capable of emitting a tunable wavelength of radiation. For example, commercially available semiconductor lasers, helium-neon lasers, carbon dioxide lasers, radiation emitting diodes, incandescent lamps, vertical cavity surface emitting lasers, edge emitting lasers, and many other known radiation emitting sources can be used as the radiation source 222. The wavelengths that are emitted by the radiation source 222 may be any suitable wavelength for performing Raman spectroscopy on the analyte. As previously described, the resonant cavities and waveguides of the Raman-enhancing structures may be configured to resonate and guide particular wavelengths of radiation.

The detector 226 receives and detects the Raman scattered radiation 228 that includes Raman scattered photons that are scattered by an analyte disposed proximate a resonant cavity of the Raman-enhancing structure. The detector 226 may include a device for determining the wavelength of the Raman scattered radiation 228, such as, for example, a monochromator, and a device for determining the intensity of the Raman scattered radiation 228, such as, for example, a photomultiplier. Typically, the Raman scattered radiation 228 is scattered in all directions relative to the Raman-enhancing structure.

Optical components 230 positioned between the source 222 and the Raman-enhancing structure can be used to collimate, filter, or focus the incident radiation 224 before the incident radiation 224 impinges on the Raman-enhancing structure. Optical components 230 positioned between the Raman-enhancing structure and the detector 226 can be used to collimate, filter, or focus the Raman scattered radiation 228. For example, a filter or a plurality of filters can be employed to prevent radiation at wavelengths corresponding to the incident radiation 224 from impinging on the detector 226, thus allowing only the Raman scattered radiation 228 to be received by the detector 226.

To perform Raman spectroscopy using the Raman spectroscopy system 220, an analyte may be provided adjacent a resonant cavity of the Raman-enhancing structure. If the resonant cavity of the Raman-enhancing structure is configured to resonate the incident electromagnetic radiation, the incident electromagnetic radiation 224 provided by the radiation source 222 may be coupled to a waveguide of the Raman-enhancing structure. The incident radiation 224 may be guided into the resonant cavity through the waveguide. The incident radiation 224 may resonate within the resonant cavity and the analyte may be subjected to the resonating radiation. Raman scattered radiation 228 scattered by the analyte may be detected by the detector 226. Optionally, the Raman-scattered radiation may be guided away from the resonant cavity towards the detector 226 in a waveguide.

If the resonant cavity of the Raman-enhancing structure is configured to resonate Raman scattered radiation, the analyte may be provided adjacent the resonant cavity and directly irradiated with incident electromagnetic radiation 224 provided by the radiation source 222. The Raman scattered radiation may couple to and resonate within the resonant cavity of the Raman-enhancing structure and may be guided to the detector 226 of the Raman spectroscopy system 220 through a waveguide.

The Raman-enhancing structure may enhance the intensity of the Raman scattered radiation 228. The wavelengths and corresponding intensity of the Raman scattered radiation 228 may be determined and used to identify and provide information about the analyte. If the Raman-enhancing structure includes a nanostructure comprising a Raman-enhancing material adjacent the analyte, the intensity of the Raman scattered radiation 228 may be further enhanced.

Figure 9:
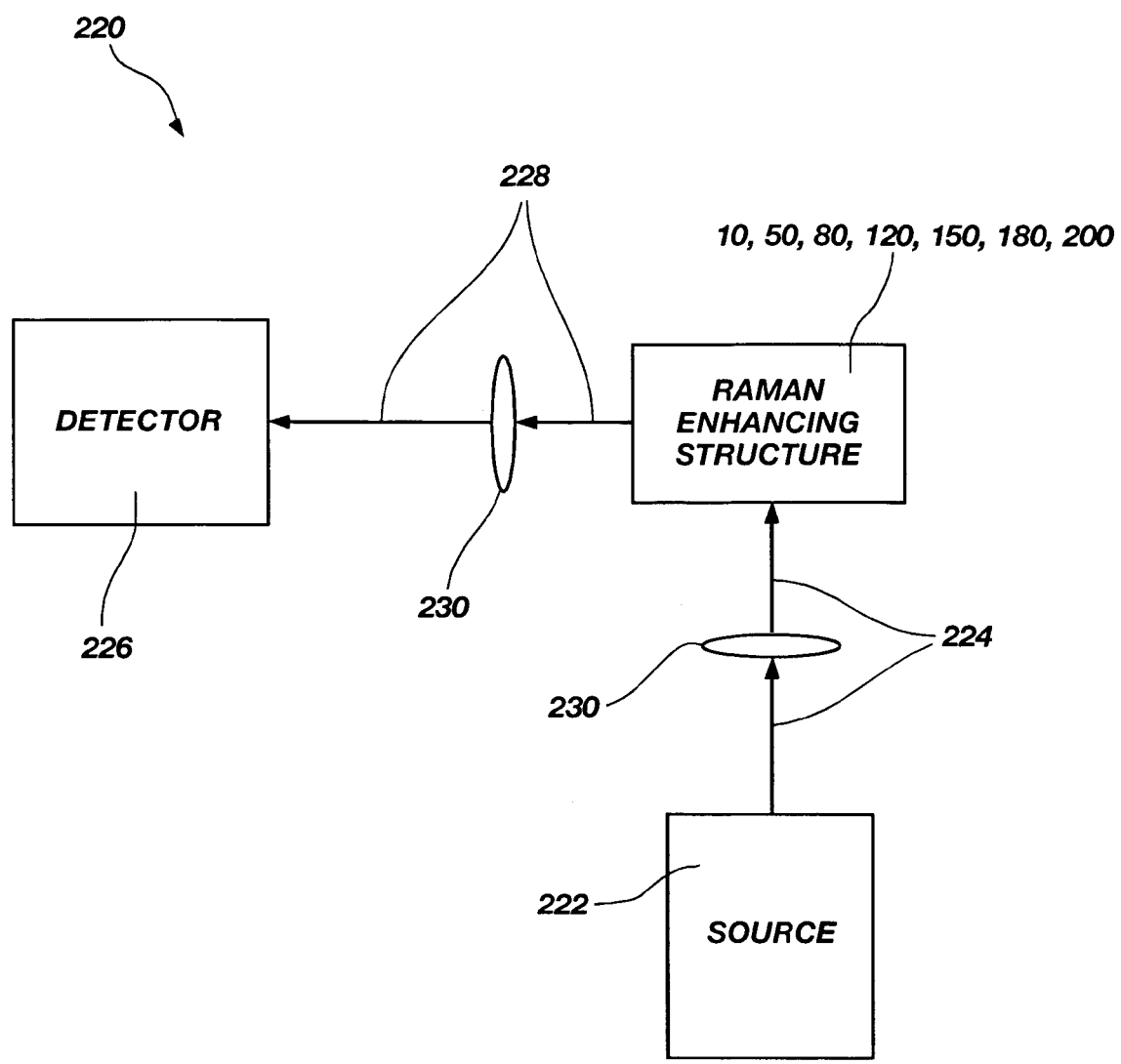
FIGS. 9-11 illustrate Raman systems that embody teachings of the present invention.
Figure 10:
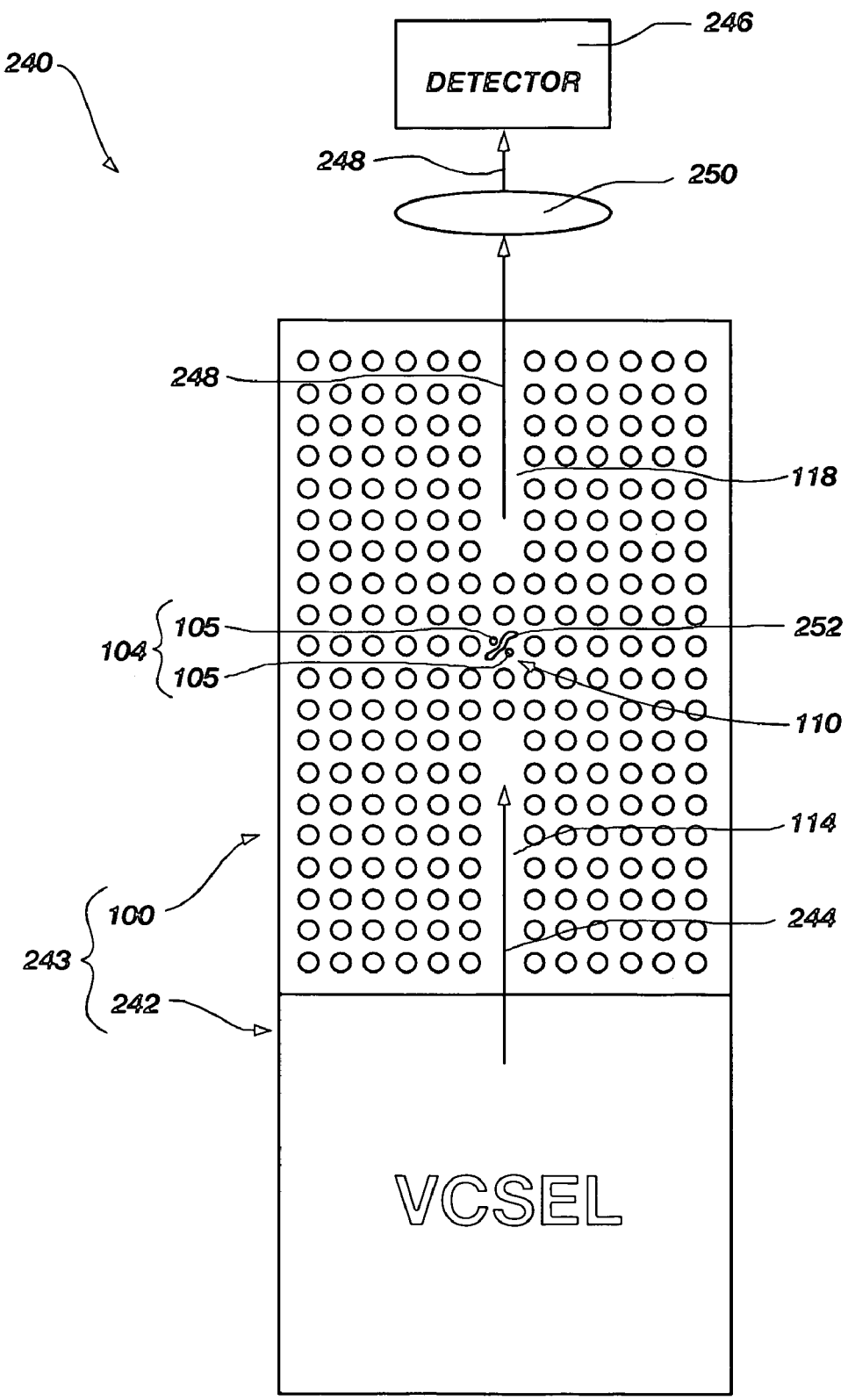

While the schematic diagram of the Raman spectroscopy system 220 shown in FIG. 9 implies that the source 222, Raman-enhancing structure, and detector 226 are three distinct structures, it should be understood that the source 222, the detector 226, or both may be integrated with the Raman-enhancing structure to provide a monolithic structure. A representative Raman spectroscopy system 240 that embodies teachings of the present invention is shown in FIG. 10. The Raman spectroscopy system 240 may include a vertical cavity surface emitting laser (VCSEL) 242 that is integrated with the Raman-enhancing structure 100 (shown in FIG. 4 and described previously herein) to form a monolithic structure 243. The incident electromagnetic radiation 244 emitted by the VCSEL 242 may be coupled to the first waveguide 114 of the Raman-enhancing structure 100. The first waveguide 114 guides the radiation 244 to the resonant cavity 110 of the Raman-enhancing structure 100. The radiation 244 may resonate within the resonant cavity 110. An analyte 252 may be provided proximate the nanoparticles 105 that include a Raman-enhancing material of the Raman-enhancing structure 100. Raman scattered radiation 248 scattered by the analyte 252 may be guided to a detector 246 using the second waveguide 118 of the Raman-enhancing structure 100. Optical components 250 may be placed between the monolithic structure 243 and the detector 246. The optical components may include, for example, lenses and filters to focus the Raman scattered radiation 248 and remove any wavelengths of electromagnetic radiation corresponding to the incident radiation 244.

In alternative embodiments of the present invention, the Raman spectroscopy system 240 may further include additional waveguides (not shown), such as, for example, optical fibers that are coupled to the second waveguide 118 of the Raman-enhancing structure 100. Such additional waveguides may be used to further guide the Raman scattered radiation 248 to the detector 246.

Figure 11:
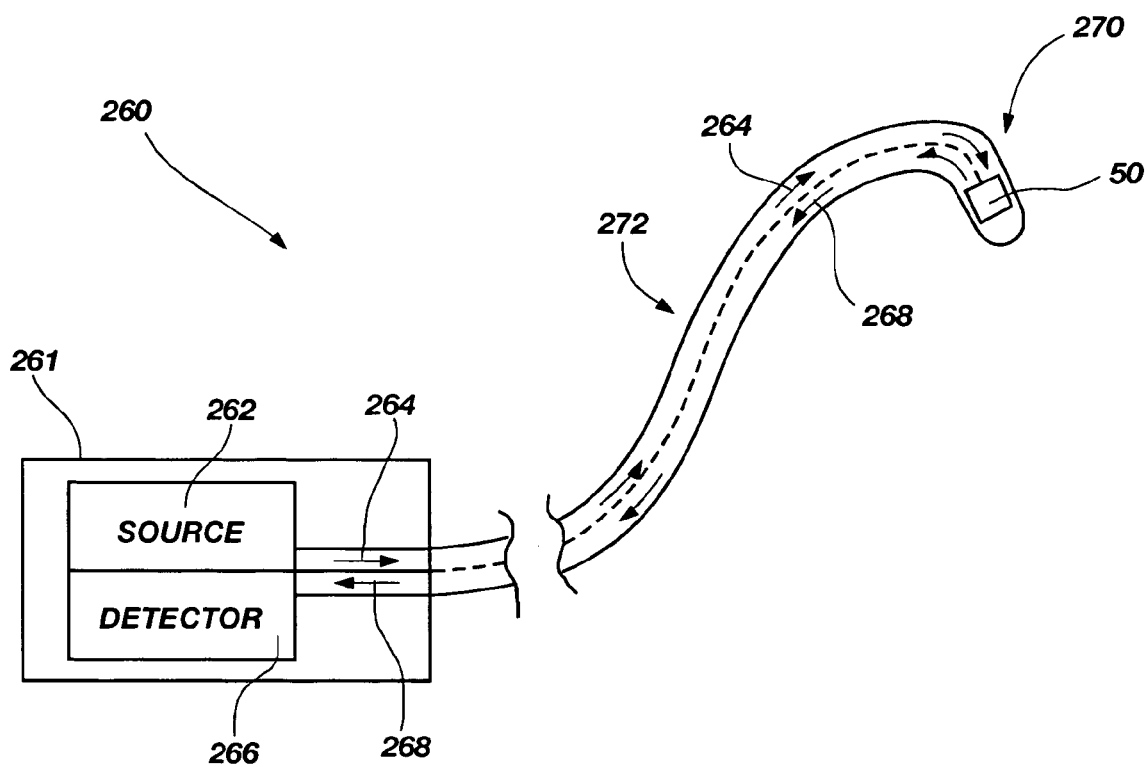

Another representative Raman spectroscopy system 260 that embodies teachings of the present invention is shown in FIG. 11. The Raman spectroscopy system 260 may include a radiation source 262 that is configured to emit incident electromagnetic radiation 264 and a radiation detector 266 that is configured to detect Raman scattered radiation. The source 262 and the detector 266 may be integrated into a portable unitary structure 261. The Raman spectroscopy system 260 further includes a probe member 270, which may include the previously described Raman-enhancing structure 50 shown in FIGS. 2A-2B. The incident electromagnetic radiation 264 emitted by the source 262 is guided to the probe member 270 and the Raman-enhancing structure 50 by optical fiber waveguides 272 that extend between the unitary structure 261 and the probe member 270. The optical fiber waveguides 272 may be coupled to the first waveguide 64 and the second waveguide 68 of the Raman-enhancing structure 50 (FIGS. 2A-2B).

In this configuration, the probe member 270 may be provided in an environment in which it is desired to perform Raman spectroscopy on an analyte (not shown). If the analyte is disposed proximate to the resonant cavity 60 and the nanoparticles 55 of the Ramen-enhancing structure 50 (FIGS. 2A-2B) and subjected to the incident radiation 264, Raman scattered radiation 268 may be scattered by the analyte. This Raman scattered radiation 268 may be guided through the first waveguide 64 or the second waveguide 68 of the Raman-enhancing structure 50 (FIGS. 2A-2B) into the optical fiber waveguides 272 extending between the unitary structure 261 and the probe member 270. The optical fiber waveguides 272 may guide the Raman scattered radiation 268 to the unitary structure 261 and the detector 266. The Raman scattered radiation 268 then may be analyzed to detect or characterize the analyte.

The Raman-enhancing structures, Raman spectroscopy systems including such structures, and methods for performing Raman spectroscopy described herein may be used to enhance the intensity of Raman scattered radiation scattered by an analyte. Furthermore, the structures, systems, and methods may be used to perform hyper-Raman spectroscopy. Furthermore, at least some of the Raman-enhancing structures, Raman spectroscopy systems including such structures, and methods for performing Raman spectroscopy described herein may be useful for detecting or analyzing two or more analytes simultaneously, which may or may not have similar Raman signals.

It should be understood that the present invention includes Raman-enhancing structures that include three-dimensional (3D) photonic crystals having resonant cavities and waveguides therein. The structures, systems, and methods described herein may be used to improve the sensitivity of currently available Raman spectroscopy systems and to improve known techniques for performing Raman spectroscopy.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A Raman-enhancing structure comprising:
   a photonic crystal comprising:
      a plurality of resonant cavities, at least two resonant cavities of the plurality of resonant cavities configured to resonate different wavelengths of radiation;
      a first line defect comprising a first waveguide coupled to the resonant cavity; and
      a second line defect comprising a second waveguide coupled to the resonant cavity; and
   a nanostructure comprising a Raman-enhancing material disposed proximate the resonant cavity of the photonic crystal;
   at least one of the first wave guide and the second wave guide being coupled to each resonant cavity of the plurality of resonant cavities.

2. A Raman-enhancing structure as recited in claim 1, wherein the resonant cavity comprises a point defect in the photonic crystal.

3. A Raman-enhancing structure as recited in claim 2, wherein the photonic crystal comprises a two-dimensional photonic crystal.

4. A Raman-enhancing structure as recited in claim 3, wherein the photonic crystal comprises a plurality of cylindrical regions dispersed periodically in an array of rows throughout a matrix, a majority of the cylindrical regions having a uniform radius, the cylindrical regions exhibiting a first dielectric constant and the matrix exhibiting a second dielectric constant that differs from the first dielectric constant.

5. A Raman-enhancing structure as recited in claim 4, wherein the resonant cavity comprises one cylindrical region of the plurality of cylindrical regions, the one cylindrical region of the resonant cavity having a radius differing from the uniform radius of the majority of the cylindrical regions.

6. A Raman-enhancing structure as recited in claim 4, wherein each cylindrical region of the plurality of cylindrical regions comprises air.

7. A Raman-enhancing structure as recited in claim 4, wherein the matrix comprises air.

8. A Raman-enhancing structure as recited in claim 4, wherein the cylindrical regions are arranged in a square lattice or a triangular lattice.

9. A Raman-enhancing structure as recited in claim 1, wherein the nanostructure comprises at least two nanoparticles disposed within the resonant cavity of the photonic crystal, each nanoparticle comprising a Raman-enhancing material.

10. A Raman-enhancing structure as recited in claim 1, further comprising an analyte disposed proximate the resonant cavity of the photonic crystal and the nanostructure.

11. A Raman-enhancing structure as recited in claim 1, wherein the resonant cavity is configured to resonate incident electromagnetic radiation.

12. A Raman-enhancing structure as recited in claim 1, wherein the resonant cavity is configured to resonate Raman-scattered radiation.

13. A Raman-enhancing structure comprising:
    a microdisk resonator;
    at least one waveguide coupled to the microdisk resonator; and
    a nanostructure comprising a Raman-enhancing material disposed proximate the microdisk resonator.

14. A Raman-enhancing structure as recited in claim 13, further comprising a plurality of microdisk resonators, each microdisk resonator being configured to resonate different wavelengths of electromagnetic radiation.

15. A Raman-enhancing structure as recited in claim 13, wherein the nanostructure comprises two or more nanoparticles, each nanoparticle comprising a Raman-enhancing material.

16. A Raman-enhancing structure as recited in claim 13, wherein the microdisk resonator is configured to resonate incident electromagnetic radiation.

17. A Raman-enhancing structure as recited in claim 13, wherein the microdisk resonator is configured to resonate Raman-scattered radiation.

18. A method for performing Raman spectroscopy comprising:
    generating incident electromagnetic radiation;
    guiding the incident electromagnetic radiation through a waveguide in a photonic crystal to a plurality of resonant cavities in the photonic crystal;

providing an analyte proximate the plurality of resonant cavities;

providing a nanostructure comprising a Raman-enhancing material proximate the plurality of resonant cavities and the analyte;

subjecting the analyte to the incident electromagnetic radiation;

resonating at least one of the incident electromagnetic radiation and Raman scattered radiation within each resonant cavity of the plurality of resonant cavities; and resonating different wavelengths of electromagnetic radiation in at least two resonant cavities of the plurality of resonant cavities;

guiding the Raman scattered radiation away from the resonant cavity through another waveguide in the photonic crystal toward a detector; and detecting the Raman scattered radiation scattered by the analyte.

19. A method for performing Raman spectroscopy comprising:

generating electromagnetic radiation;

guiding the electromagnetic radiation through a waveguide to a microdisk resonator;

resonating the electromagnetic radiation within the microdisk resonator;

providing an analyte proximate the microdisk resonator;

subjecting the analyte to the resonating electromagnetic radiation; and detecting Raman scattered radiation scattered by the analyte.

20. A method as recited in claim 19, further comprising providing a nanostructure comprising a Raman-enhancing material proximate the microdisk resonator and the analyte.

21. A method as recited in claim 20, further comprising:

guiding incident electromagnetic radiation through the waveguide to a plurality of microdisk resonators;

resonating at least one of the incident electromagnetic radiation and Raman scattered radiation within each microdisk resonator of the plurality of microdisk resonators; and resonating different wavelengths of radiation within at least two microdisk resonators of the plurality of microdisk resonators.

* * * * *

UNITED STATES PATENT AND TRADEMARK OFFICE
CERTIFICATE OF CORRECTION

PATENT NO. : 7,466,407 B2 Page 1 of 1
APPLICATION NO. : 11/413877
DATED : December 16, 2008
INVENTOR(S) : Sean M. Spillane et al.

It is certified that error appears in the above-identified patent and that said Letters Patent is hereby corrected as shown below:

In column 19, line 65, in Claim 1, delete "wave guide" and insert -- waveguide --, therefor.

In column 19, lines 65-66, in Claim 1, delete "wave guide" and insert -- waveguide --, therefor.

Signed and Sealed this

Twenty-first Day of July, 2009

JOHN DOLL
*Acting Director of the United States Patent and Trademark Office*